United States Patent
Zhu et al.

(10) Patent No.: US 12,331,435 B2
(45) Date of Patent: Jun. 17, 2025

(54) MULTI-FUNCTIONAL ELECTRONIC TEXTILES EMPLOYING SILVER NANOWIRE COMPOSITE SENSORS AND RELATED METHODS

(71) Applicant: North Carolina State University, Raleigh, NC (US)

(72) Inventors: Yong Zhu, Apex, NC (US); Shanshan Yao, Coram, NY (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 153 days.

(21) Appl. No.: 17/232,095

(22) Filed: Apr. 15, 2021

(65) Prior Publication Data
US 2021/0324550 A1    Oct. 21, 2021

Related U.S. Application Data

(60) Provisional application No. 63/011,262, filed on Apr. 16, 2020.

(51) Int. Cl.
| | |
|---|---|
| *D03D 1/00* | (2006.01) |
| *A41D 1/00* | (2018.01) |
| *A61B 5/00* | (2006.01) |
| *B82Y 30/00* | (2011.01) |
| *D01F 8/04* | (2006.01) |
| *D06M 10/06* | (2006.01) |

(52) U.S. Cl.
CPC ............ *D03D 1/0088* (2013.01); *B82Y 30/00* (2013.01); *D01F 8/04* (2013.01); *D06M 10/06* (2013.01); *A41D 1/002* (2013.01); *A61B 5/6804* (2013.01); *D10B 2401/16* (2013.01)

(58) Field of Classification Search
None
See application file for complete search history.

(56) References Cited

U.S. PATENT DOCUMENTS

| | | | |
|---|---|---|---|
| 2016/0052131 A1* | 2/2016 | Lessing | B25J 15/12 361/679.01 |
| 2018/0020936 A1* | 1/2018 | Kwon | H01B 5/14 600/388 |
| 2022/0340726 A1 | 10/2022 | Zhu et al. | |

OTHER PUBLICATIONS

Ankhili et al., "Washable and Reliable Textile Electrodes Embedded into Underwear Fabric for Electrocardiogramonitoring," Materials, vol. 11, No. 256, pp. 1-11 (2018).

(Continued)

*Primary Examiner* — Shawn Mckinnon
(74) *Attorney, Agent, or Firm* — Jenkins, Taylor & Hunt, P.A.

(57) ABSTRACT

Multi-functional electronic textiles employing nanocomposite pattern elements and related methods are provided. An exemplary method for producing a textile product with an integrated electrical device includes applying conductive nanowires to a substrate to form a conductive nanowire network on the substrate and applying a thermoplastic elastomer to the nanowire network to form a nanocomposite layer on top of the substrate. The method also includes cutting the nanocomposite layer into a desired pattern to form an electrical device and transferring the electrical device from the substrate onto a textile fabric.

9 Claims, 26 Drawing Sheets

(56) References Cited

OTHER PUBLICATIONS

Cao et al., "Screen-Printed Washable Electronic Textiles as Self-Powered Touch/Gesture Tribo-Sensors for Intelligent Human-Machine Interaction," ACS Nano, vol. 12, pp. 5190-5196 (2018).
Cui et al., "Electrohydrodynamic printing of silver nanowires for flexible and stretchable electronics," Nanoscale, vol. 10, pp. 6806-6811 (2018).
Heo et al., "Recent Progress of Textile-Based Wearable Electronics: A Comprehensive Review of Materials, Devices, and Applications," Small, vol. 14, pp. 1-16 (2018).
Huang et al., "Three-dimensional integrated stretchable electronics," Nature Electronics, vol. 1, pp. 473-480 (Aug. 2018).
Huang et al., "Inkjet Printing of Silver Nanowires for Stretchable Heaters," ACS Appl. Nano Mater, vol. 1, pp. 4528-4536 (2018).
Rahimi et al., "Laser-Enabled Processing of Stretchable Electronics on a Hydrolytically Degradable Hydrogel," Adv. Healthcare Mater, vol. 7, pp. 1-14 (2018).
Son et al., "An integrated self-healable electronic skin system fabricated via dynamic reconstruction of a nanostructured conducting network," Nature Nanotechnology, vol. 13, pp. 1057-1065 (Nov. 2018).
Sun et al., "Gas-Permeable Multifunctional on-Skin Electronics Based on Laser-Induced Porous Graphene and Sugar-Templated Elastomer Sponges," Adv. Mater, vol. 30, pp. 1-8 (2018).
Tao et al., "Bluetooth Low Energy-Based Washable Wearable Activity Motion and Electrocardiogram Textronic Monitoring and Communicating System," Adv. Mater. Technol, vol. 3, pp. 1-6 (2018).
Wang et al., "Mechano-Based Transductive Sensing for Wearable Healthcare," Small, vol. 14, pp. 1-11 (2018).
Yao et al., "A Novel Finger Kinematic Tracking Method Based on Skin-Like Wearable Strain Sensors," IEEE Sensors Journal, vol. 18, No. 7, pp. 3010-3015 (2018).
Yu et al., "Highly Stretchable, Weavable, and Washable Piezoresistive Microfiber Sensors," ACS Appl. Mater. Interfaces, vol. 10, pp. 12773-12780 (2018).
Wang et al., "A Highly Stretchable Transparent Self-Powered Triboelectric Tactile Sensor with Metallized Nanofibers for Wearable Electronics," Adv. Mater, vol. 30, pp. 1-8 (2018).
Wills et al., "Additive process for patterned metallized conductive tracks on cotton with applications in smart textiles," The Journal of Textile Institute, vol. 109, No. 2, pp. 1-11 (2018).
Yao et al., "Nanomaterial-Enabled Wearable Sensors for Healthcare," Adv. Healthcare Mater, vol. 7, pp. 1-27 (2018).
Gong et al., "One-Dimensional Nanomaterials for Soft Electronics," Adv. Electron. Mater, vol. 3, pp. 1-29 (2017).
Huang et al., "Gravure Printing of Water-based Silver Nanowire ink on Plastic Substrate for Flexible Electronics," Scientific Reports, vol. 8, pp. 1-10 (2018).
Jin et al., "Enhancing the Performance of Stretchable Conductors for E-Textiles by Controlled Ink Permeation," Adv. Mater, vol. 29, pp. 1-8 (2017).
Kim et al., "Rubbery electronics and sensors from intrinsically stretchable elastomeric composites of semiconductors and conductors," Sci. Adv. vol. 3, pp. 1-8 (Sep. 8, 2017).
Miyamoto et al., "Inflammation-free, gas-permeable, lightweight, stretchable on-skin electronics with nanomeshes," Nature Nanotechnology, vol. 12, pp. 907-914 (Sep. 2017).
Tao et al., "How to Make Reliable, Washable, and Wearable Textronic Devices," Sensors, vol. 17, No. 673, pp. 1-16 (2017).
Yao et al., "A Wearable Hydration Sensor with Conformal Nanowire Electrodes," Adv. Healthcare Mater, vol. 6, pp. 1-8 (2017).
Yao et al., "Soft electrothermal actuators using silver nanowire heaters," Nanoscale, vol. 9, pp. 1-10 (2017).
Amjadi et al., "Stretchable, Skin-Mountable, and Wearable Strain Sensors and Their Potential Applications: A Review," Adv. Funct. Maater., vol. 26, pp. 1678-1698 (2016).

Gao et al., "Fully integrated wearable sensor arrays for multiplexed in situ perspiration analysis," Nature, vol. 529, pp. 509-526 (Jan. 28, 2016).
Han et al., "Mechanically Reinforced Skin-Electronics with Networked Nanocomposite Elastomer," Adv. Mater, vol. 28, pp. 10257-10265 (2016).
Khan et al., "Monitoring of Vital Signs witih Flexible and Wearable Medical Devices," Adv. Mater., vol. 28, pp. 4373-4395 (2016).
Lee et al., "A graphene-based electrochemical device with thermoresponsive microneedles for diabetes monitoring and therapy," Nature Nanotechnology, vol. 11, pp. 1-9 (Jun. 2016).
Liang et al., "A Water-Based Silver-Nanowire Screen-Print Ink for the Fabrication of Stretchable Conductors and Wearable Thin-Film Transistors," Adv. Mater, vol. 28, pp. 5986-5996 (2016).
Nakamoto et al., "Stretchable Strain Sensor with Anistrophy and Application for Joint Angle Measurement," IEEE Sensors Journal, vol. 16, No. 10, pp. 3572-3579 (May 5, 2016).
Suikkola et al., "Screen-Printing Fabrication and Characterization of Stretchable Electronics," Scientific Reports, vol. 6, pp. 1-8 (2016).
Yao et al., "Nanomaterial-Enabled Dry Electrodes for Electrophysiological Sensing: A Review," JOM, vol. 68, No. 4, pp. 1145-1155 (2016).
Yokus et al., "Printed Stretchable Interconnects for Smart Garments: Design, Fabrication, and Characterization," IEEE Sensors Journal, vol. 16, No. 22, pp. 7967-7976 (Nov. 15, 2016).
Zhao et al., "Machine-Washable Textile Triboelectric Nanogenerators for Effective Human Respiratory Monitoring through Loom Weaving of Metallic Yarns," Adv. Mater, vol. 28, pp. 10267-10274 (2016).
Cui et al., "Design and operation of silver nanowire based flexible and stretchable touch sensors," J. Mater. Res, vol. 30, No. 1, pp. 79-85 (2015).
Hsu et al., "Personal Thermal Management by Metallic Nanowire-Coated Textile," Nano Lett., vol. 15, pp. 365-371 (2015).
Lim et al., "Transparent and Stretchable Interactive Human Machine Interface Based on Patterned Graphene Heterostructures," Adv. Funct. Mater., vol. 25, pp. 375-383 (2015).
Malanga et al., "Mechanisms and efficacy of heat and cold therapies for musculoskeletal injury," Postgraduate Medicine, vol. 127, No. 1, pp. 1-10 (2015).
Matsuhisa et al., "Printable elastic conductors with a high conductivity for electronic textile applications," Nature Communications, vol. 6, No. 7461, pp. 1-11 (Jun. 25, 2015).
Yao et al., "Nanomaterial-Enabled Stretchable Conductors: Strategies, Materials and Devices," Adv. Mater, vol. 27, pp. 1480-1511 (2015).
Castano et al., "Smart fabric sensors and e-textile technologies: a review," Smart Mater. Struct, vol. 23, pp. 1-28 (2014).
Fan et al., "Fractal design concepts for stretchable electronics," Nature Communications, vol. 5, pp. 1-8 (2014).
Dehghan et al., "The Efficacy of Thermotherapy and Cryotherapy on Pain Relief in Patients with Acute Low Back Pain, A Clinical Trial Study," Journal of Clinical and Diagnostic Research, vol. 8, No. 9, pp. 1-4 (Sep. 2014).
Jang et al., "Rugged and breathable forms of stretchable electronics with adherent composite substrates for transcutaneous monitoring," Nature Communications, vol. 5, pp. 1-10 (Sep. 3, 2014).
Langley et al., "Metallic nanowire networks: effects of thermal annealing on electric resistance," Nanoscale, vol. 6, pp. 1-9 (2014).
Lee et al., "Direct Alignment and Patterning of Silver Nanowires by Electrohydrodynamic Jet Printing," Small, vol. 10, No. 19, pp. 3918-3922 (2014).
Song et al., "Stretchable and Reversibly Deformable Radio Frequency Antennas Based on Silver Nanowires," ACS Appl. Mater. Interfaces, vol. 6, pp. 4248-4253 (2014).
Yao et al., "Wearable multifunctional sensors using printed stretchable conductors made of silver nanowires," Nanoscale, vol. 6, pp. 1-8 (2014).
Zeng et al., "Fiber-Based Wearable Electronics: A Review of Materials, Fabrication, Devices, and Applications," Adv. Mater, vol. 26, pp. 1-27 (2014).

(56) References Cited

OTHER PUBLICATIONS

Vervust et al., "Integration of stretchable and washable electronic modules for smart textile applications," The Journal of Textile Institute, vol. 103, No. 10, pp. 1-13 (2012).
Xu et al., "Highly Conductive and Stretchable Silver Nanowire Conductors," Adv. Mater., vol. 24, pp. 5117-5122 (2012).
Kim et al., "Epidermal Electronics," Science, vol. 333, No. 6044, pp. 1-7 (Aug. 12, 2011).
Tokuno et al., "Fabrication of Silver Nanowire Transparent Electrodes at Room Temperature," Nano Res., vol. 4, No. 12, pp. 1215-1222 (2011).
Rogers et al., "Materials and Mechanics for Stretchable Electronics," Science, vol. 327, pp. 1-6 (Mar. 26, 2010).
Okada et al., "The influence of hot pack therapy on the blood flow in masseter muscles," Journal of Oral Rehabilitation, vol. 32, pp. 480-486 (2005).
Chen, et al. "Electronic Muscles and Skins: A Review of Soft Sensors and Actuartors", Chem. Rev., vol. 117, pp. 11239-11268 (2017).
Liu, et al., "Nature-Inspired Structural Materials for Flexible Electronic Devices", Chem. Rev., vol. 117, pp. 12893-12941 (2017).
Yao, et al., "Nanomaterial-Enabled Wearable Sensors for Healthcare", Adv. Healthcare Mater., 7, 1700889 (2018).
Kim, et al., "Flexible and Stretchable Electronics for Biointegrated Devices" Annu. Rev. Biomed. Eng., vol. 14, pp. 113-128 (2012).
Yao, et al., "Nanomaterial-Enabled Flexible and Stretchable Sensing Systems: Processing, Integration, and Applications", Adv. Mater., e1902343 (2019).
Kim, et al., "Epidermal Electronics", Science, vol. 333, pp. 838-843 (2011).
Trung, et al., "Flexible and Stretchable Physical Sensor Integrated Platforms for Wearable Human-Activity Monitoring and Personal Healthcare", Adv. Mater., vol. 28, pp. 4338-4372 (2016).
Kaltenbrunner, et al., "An Ultra-Lightweight Design for Imperceptible Plastic Electronics", Nature, vol. 499, pp. 458-463 (2013).
Lipomi, et al., "Skin-Like Pressure and Strain Sensors Based on Transparent Elastic Films of Carbon Nanotubes", Nat. Nanotechnol, vol. 6, pp. 788-792 (2011).
Yeo, et al., "Multifunctional Epidermal Electronics Printed Directly Onto the Skin", Adv. Mater., vol. 25, pp. 2773-2778 (2013).
Gong, et al., "Multiscale Soft-Hard Interface Design for Flexible Hybrid Electronics", Adv. Mater., 1902278 (2019).
Kim, et al., "Hygroscopic Auxetic On-Skin Sensors for Easy-to-Handle Repeated Daily Use", ACS Appl. Mater Interfaces, vol. 10, pp. 40141-40148 (2018).
Yang, et al., ""Cut-and-Paste" Manufacture of Multiparametric Epidermal Sensor Systems", Adv. Mater., vol. 27, pp. 6423-6430 (2015).
Kim, et al., "Highly Conformable, Transparent Electrodes for Epidermal Electronics", Nano Lett., vol. 18, pp. 4531-4540 (2018).
You, et al., "Stretchable E-Skin Apexcardiogram Sensor", Adv. Mater., vol. 28, pp. 6359-6364 (2016).
Gong, et al., "Local Crack-Programmed Gold Nanowire Electronic Skin Tattoos for In-Plane Multisensor integration", Adv. Mater., vol. 31, e1903789 (2019).
Miyamoto, et al., "Inflammation-Free, Gas-Permeable, Lightweight, Stretchable On-Skin Electronics with Nanomeshes", Nat. Nanotechnol., vol. 12, pp. 907-913 (2017).
Sun, et al., "Gas-Permeable, Multifunctional On-Skin Electronics Based on Laser-Induced Porous Graphene and Sugar-Templated Elastomer Sponges", Adv. Mater., vol. 30, e1804327 (2018).
Fan, et al., "Highly Robust, Transparent, and Breathable Epidermal Electrode" ACS Nano, 12, pp. 9326-9332 (2018).
Cai, et al., "Warming Up Human Body by Nanoporous Metallized Polyethylene Textile", Nat. Commun., 8, 496 (2017).
Bai, et al., "Breath Figure Arrays: Unconventional Fabrications, Functionalizations, and Applications", Angew. Chem. Int. Ed. Engl., 52, pp. 12240-12255 (2013).
Zhang, et al., "Breath Figure: A Nature-Inspired Preparation Method for Ordered Porous Films", Chem. Rev., 115, pp. 9801-9868 (2015).
Ponnusamy, et al., "In Vitro Degradation and Release Characteristics of Spin Coated Thin Films of PLGA with A "Breath Figure" Morphology", Biomatter, 2, pp. 77-86 (2012).
Yao, et al., "Multifunctional Electronic Textiles Using Silver Nanowire Composites", ACS Appl. Mater. Interfaces, 11, pp. 31028-31037 (2019).
Cui, et al., "Tailoring the Temperature Coefficient of Resistance of Silver Nanowire Nanocomposites and Their Application as Stretchable Temperature Sensors", ACS Appl. Mater. Interfaces, 11, pp. 17836-17842 (2019).
Standard Test Methods for Water Vapor Transmission of Materials. ASTM International: West Conshohocken, PA, pp. 1-12 (2016).
Xu, et al., "Wavy Ribbons of Carbon Nanotubes for Stretchable Conductors", Adv. Funct. Mater., 22, pp. 1279-1283 (2012).
Zhu, et al., "Buckling of Aligned Carbon Nanotubes as Stretchable Conductors: A New Manufacturing Strategy", Adv. Mater., 24, pp. 1073-1077 (2012).
Xu, et al., "Highly Conductive and Stretchable Silver Nanowire Conductors", Adv. Mater., 24, pp. 5117-5122 (2012).
Yao, et al., "Nanomaterial-Enabled Stretchable Conductors: Strategies, Materials and Devices", Adv. Mater., 27, pp. 1480-1511 (2015).
Jin, et al., "Microstructural Origin of Resistance-Strain Hysteresis in Carbon Nanotube Thin Film Conductors", Proc. Natl. Acad. Sci., 115, pp. 1986-1991 (2018).
Myers, et al., "Wearable Silver Nanowire Dry Electrodes for Electrophysiological Sensing", RSC Adv., 5, pp. 11627-11632 (2015).
Barrett, et al., "Projected-Capacitive Touch Technology", Inf. Disp., 26, pp. 16-21 (2010).
Nelson, C. Hello Capacitive Touch. https://learn.adafruit.com/circuit-playground-fruit-drums/hello-capacitive-touch (accessed Dec. 12, 2019).
Touch Sensor Application Note. https://github.com/espressif/esp-iot-solution/blob/master/documents/touch_pad_solution/touch_sensor_design_en.md (accessed Mar. 2020).
Sun, et al., "Large-Scale Synthesis of Uniform Silver Nanowires Through a Soft, Self-Seeding, Polyol Process", Adv. Mater., 14, pp. 833-837 (2002).
Zhu, et al. "Size Effects on Elasticity, Yielding, and Fracture of Silver Nanowires:In Situ Experiments", Phys. Rev. B: Condens. Matter, 85, 045443 (2012).
Wan, et al., "Pore Shape of Honeycomb-Patterned Films: Modulation and Interfacial Behavior", J. Phys. Chem. B, 116, pp. 40-47 (2012).
Restriction Requirement for U.S. Appl. No. 17/728,182 (Apr. 25, 2025).

\* cited by examiner

MULTI-FUNCTIONAL ELECTRONIC TEXTILES EMPLOYING SILVER NANOWIRE COMPOSITE SENSORS AND RELATED METHODS

CROSS-REFERENCE TO RELATED APPLICATIONS

This application claims benefit of U.S. Provisional Patent Application Ser. No. 63/011,262, filed Apr. 16, 2020, the disclosure of which is incorporated by reference herein in its entirety.

GOVERNMENT INTEREST

This invention was made with government support under Grant No. 1728370 awarded by the National Science Foundation (NSF). The government has certain rights in the invention.

TECHNICAL FIELD

The subject matter described herein relates to electronic textiles comprising nanocomposite materials and the manufacturing of the same. More specifically, the subject matter relates to multi-functional electronic textile materials employing nanowire nanocomposites and related methods.

BACKGROUND

Currently, textiles represent an appealing platform for continuous wearable applications due to the remarkable combination of breathability, compliance, and comfort for long term wear. However, use of these textile fabrics may be problematic in instances where attempts are made to integrate electrical components into the textile material or clothing. Notably, these electronic textiles (E-textiles) can be constructed by directly knitting, weaving, or embroidering conductive fibers, or by coating, printing or laminating conductive materials onto the fibers and/or fabrics. Nonetheless, these technologies face specific challenges such as low conductivity, limited patterning resolution, poor electromechanical stability, increased elastic modulus of the textile material, and complex fabrication processes. In spite of recent advances, E-textiles are still limited by a lack of robust fabrication techniques for integrating multifunctionality onto textile materials in a simple, versatile, high-resolution, and scalable manner. Moreover, the washability, permeability, and sturdiness characteristics of these e-textile materials can be quickly compromised depending on the application or adhering process that is utilized to produce the integrated product.

Accordingly, there exists a need for improved multi-functional electronic textiles employing nanowire nanocomposites and related methods.

SUMMARY

According to one aspect, the subject matter described herein relates to an exemplary method for producing a textile product with an integrated electrical device that includes applying conductive nanostructures to a substrate to form a conductive nanostructure network on the substrate, applying a thermoplastic elastomer to the nanostructure network to form a nanocomposite layer on top of the substrate, cutting the nanocomposite layer into a pattern to form an electrical device, and transferring the electrical device from the substrate onto a textile material to form an electronically integrated textile product.

According to another aspect, the subject matter described herein relates to an exemplary textile material product with an integrated electrical device, the textile material product comprising a textile material and an electrical device bonded to the textile material, wherein the electrical device comprises a network of conductive nanostructures coated with a thermoplastic elastomer to form a nanocomposite layer, which is cut into a pattern to form an electrical device, and wherein the electrical device is bonded to the textile material to form an electronically integrated textile product.

According to another aspect, the subject matter described herein relates to an exemplary electrical device patch for bonding to a textile material, the electrical device patch comprising a conductive nanostructure network and a thermoplastic elastomer coating located on the conductive nanostructure network to form a nanocomposite layer, wherein the nanocomposite layer is cut into a desired pattern to form an electrical device which is transferrable onto a textile material.

BRIEF DESCRIPTION OF THE DRAWINGS

The subject matter described herein will now be explained with reference to the accompanying drawings of which.

DETAILED DESCRIPTION

Figure 1:
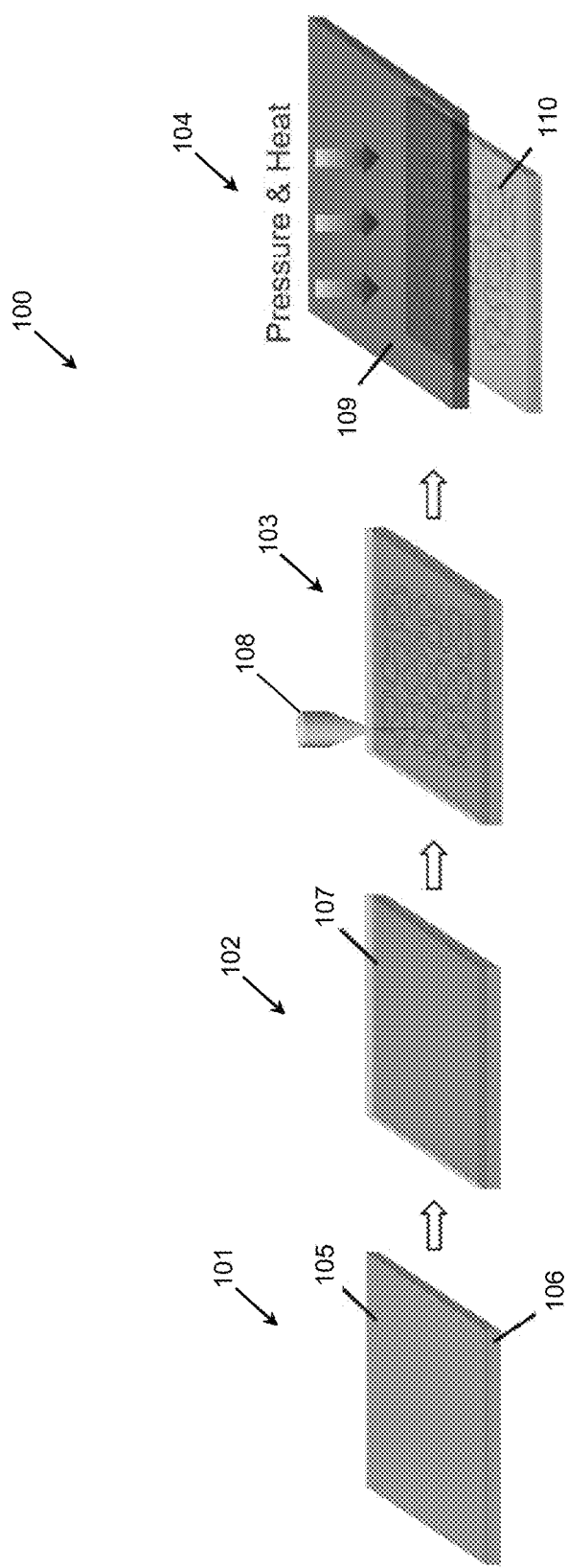
FIG. 1 depicts an exemplary fabrication process of a nanocomposite pattern element according to an embodiment of the subject matter described herein.

It will be understood that various details of the presently disclosed subject matter may be changed without departing from the scope of the presently disclosed subject matter. Furthermore, the foregoing description is for the purpose of illustration only, and not for the purpose of limitation. As indicated above, textiles represent an appealing platform for continuous wearable applications due to the exceptional combination of breathability, compliance, and comfortableness for long-term wear. In some embodiments, the disclosed subject matter presents a mechanically and electrically robust integration of nanocomposites with textiles by laser scribing and heat press lamination. The simple and scalable integration technique enables the utilization of multifunctional electronic textiles (E-textiles) without compromising the stretchability, wearability and washability of the underlying textile materials or fabrics. For example, some textile-integrated patterns may exhibit small linewidth (135 µm), low sheet resistance (0.2 Ω/sq), low Young's modulus, good washability, and good electromechanical performance up to 50% strain, which is desirable for wearable and user-friendly electronic textile materials. To demonstrate the potential utility of an example embodiment, an integrated textile patch comprising four dry electrophysiological electrodes, a capacitive strain sensor, and a wireless resistive heater can be configured for electrophysiological sensing, motion tracking, and thermotherapy functionalities, respectively. Although four electrodes are utilized in this example, any number of electrodes (i.e., one or more electrodes) can be utilized without departing from the scope of the disclosed subject matter. In some embodiments, the integrated textile patch can include one or more sensors/devices including, but not limited to, a capacitive strain gauge, an angular velocity sensor, a heater, an electrocardiography (ECG) sensor, and/or an electromyography (EMG) sensor. Beyond the applications demonstrated herein, the disclosed subject matter paves the way for various other wearable applications in many use cases, including healthcare, activity tracking, rehabilitation, and human-machine interactions.

Wearable electronics that are able to conform to curvilinear and complex skin surfaces to continuously monitor an individual's activities offer new opportunities in the tracking of wellness, treatment of illness, and interactions with smart devices. Numerous wearable devices have been developed, including a variety of sensors, displays, energy harvesting and storage devices, and drug delivery systems. Compared to wearable devices dedicated to and/or equipped with a single function, integrated multifunctional wearable devices may be configured for a comprehensive tracking of physiological parameters, multimodal electronic skin, interactive human machine interfaces, and on-chip therapeutic treatment on a minimized platform. Significant progress has been made towards the realization of multifunctional wearable devices on elastomer substrates. Representative examples of such devices include epidermal electronics, multiplexed sweat sensing system, wearable diabetes monitoring and therapy system, and gas permeable stretchable on-skin electronics. Being soft, lightweight, breathable, and comfortable, textiles provide an ideal platform for wearable devices that can be worn long term on a daily basis. However, multifunctional wearable devices that are built on textile substrates are relatively unexplored.

Electronic textiles (E-textiles) have been realized using a variety of fabrication methods. E-textiles can be constructed by directly knitting, weaving, embroidering conductive fibers, or by coating, printing, bonding, or laminating conductive materials onto the fibers or fabrics. However, these technologies face challenges such as low conductivity, limited patterning resolution, poor electromechanical stability, increased elastic modulus of the textiles, and complex fabrication processes. In spite of noteworthy advances, E-textiles are currently limited by the lack of robust fabrication techniques to integrate multifunctionality onto textiles in a simple, versatile, high-resolution, and scalable way.

The disclosed subject matter addresses these challenges by employing soft electronic materials, deformable structures, and efficient processes to enable multifunctional E-textiles without losing the wearability, washability, and comfortableness of the underlying textile materials. Although the following subject matter discloses the use of an example silver nanowire (AgNW) network, other nanostructure networks comprising different nanostructures and/or metals can be utilized without departing from the scope of the disclosed subject matter.

In some embodiments, a nanocomposite, such as silver nanowire (AgNW) and thermoplastic elastomer nanocomposite (e.g., AgNW/TPU nanocomposite), can be cut into a desired pattern to form an electrical device via a laser scribing patterning process and is subsequently bonded to a fabric material through a heat press lamination process. During the laser scribing patterning process, arbitrary patterns with high resolution can be generated without the need of masks or stencils. Moreover, the heat press lamination process offers a facile way to laminate patterned nanostructures (e.g., the patterned AgNW nanocomposites) with strong bonding onto textile materials while maintaining the inherent electrical properties. The disclosed integration process results in highly conductive, stretchable, compliant and washable patterns on textile materials, which form the building blocks for textile-based smart devices. Based on the textile laminated patterns, an integrated patch that incorporates dry electrodes for electrophysiological sensing, a capacitive strain gauge for motion sensing, and a wireless resistive heater for thermotherapy can be demonstrated.

In FIG. 1, an exemplary fabrication process 100 is depicted. Notably, fabrication process 100 may involve the application of the nanocomposite pattern element to a textile material or fabric (e.g., textile integration of an E-textile). As used herein, a textile material may include any textile component, such as fabrics, sports tapes, clothes, sports sleeves, wristbands, shoulder and knee braces, and the like. Returning to FIG. 1, process 100 begins at step 101 where an AgNW solution 105 may be uniformly coated onto a glass substrate 106 with a Meyer rod. After evaporating the solvent, percolative networks of AgNWs are formed (e.g., a nanostructure network) on glass substrate 106. Notably, the AgNW solution 105 contains a multitude of nanostructures that includes, but is not limited to, a plurality of nanowires, a plurality of nanotubes, a plurality of nanoflakes, a plurality of nanoparticles, a plurality of nanorods, and/or a plurality of nanobeads. Further, while the following disclosure describes the nanostructures and/or nanowires as being made of silver, other metals can be utilized (e.g., gold or copper) without departing from the scope of the disclosed subject matter. Afterwards process 100 proceeds to step 102 where a thermoplastic elastomer solution 107, such as a thermoplastic polyurethane (TPU) solution, can be applied (e.g., spin-coated, poured, etc.) on top of the AgNW nanostructure networks. The thermoplastic elastomer solution 107 may be applied in any fashion in which the nanostructure network(s) is infiltrated and/or encapsulated by the thermoplastic elastomer. Afterwards, the thermoplastic elastomer portion of the encapsulated nanostructure network may be cured to collectively form a nanocomposite layer on top of the substrate. For example, curing may involve air drying or heating the thermoplastic elastomer such that the material solidifies around the nanostructure network(s).

Figure 2:
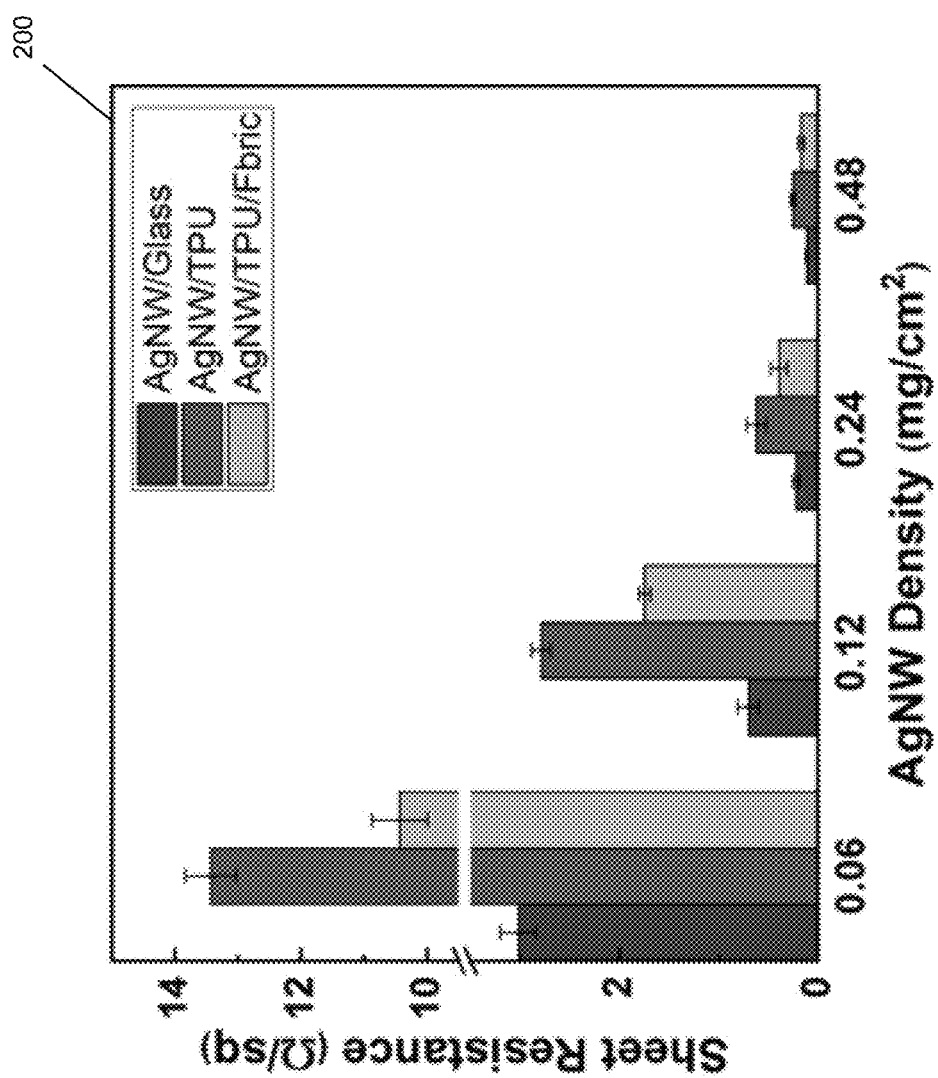
FIG. 2 is an exemplary bar graph depicting the comparison of sheet resistance of various nanostructures on a glass substrate according to an embodiment of the subject matter described herein.

In step 103 of FIG. 1, the nanocomposite layer is cut into one or more patterns. In some embodiments, to form the desired patterns (e.g., nanocomposite pattern element), the AgNW/TPU nanocomposites may be subjected to a laser scribe device 108 that is configured for laser scribing according to a two dimensional (2D) CAD drawing. This direct patterning method of AgNW based conductors can achieve high resolution (e.g., 135 μm) and high throughput, complementary to other direct writing methods. For example, ink jet printing requires the AgNWs to be shortened to avoid nozzle clogging during printing, which however sacrifices the advantage of nanowires. Other printing methods, including gravure, screen printing, and electrohydrodynamic (EHD) printing, often require the introduction of additives to adjust the viscosity of the ink and an extra water rinsing step to remove the additives, which can peel off and damage the printed patterns. The selection of TPU to embed the AgNWs (i.e., nanostructures networks) has several advantages: 1) TPU solution can blend well into the AgNW percolation networks due to its good wettability of AgNWs and the resulting AgNW/TPU nanocomposites maintain excellent electrical conductivity (e.g., as shown in FIG. 2); 2) TPU is a stretchable, hot-melt adhesive that can form reliable bonding to textile materials. At step 104 of FIG. 1, the AgNW/TPU patterns 110 can then be heat-pressed at a temperature ranging approximately between 100° C. and 150° C. to transfer the nanocomposite layer from the glass substrate onto a stretchable fabric material 109. In some embodiments, the AgNW/TPU patterns 110 are transferred via a heat-press temperature of 140° C. The resulting electronically integrated textile product (e.g., the textile-integrated AgNW/TPU patterns) are highly conductive, compliant, stretchable and washable, ideal for E-textile applications.

Figure 3:
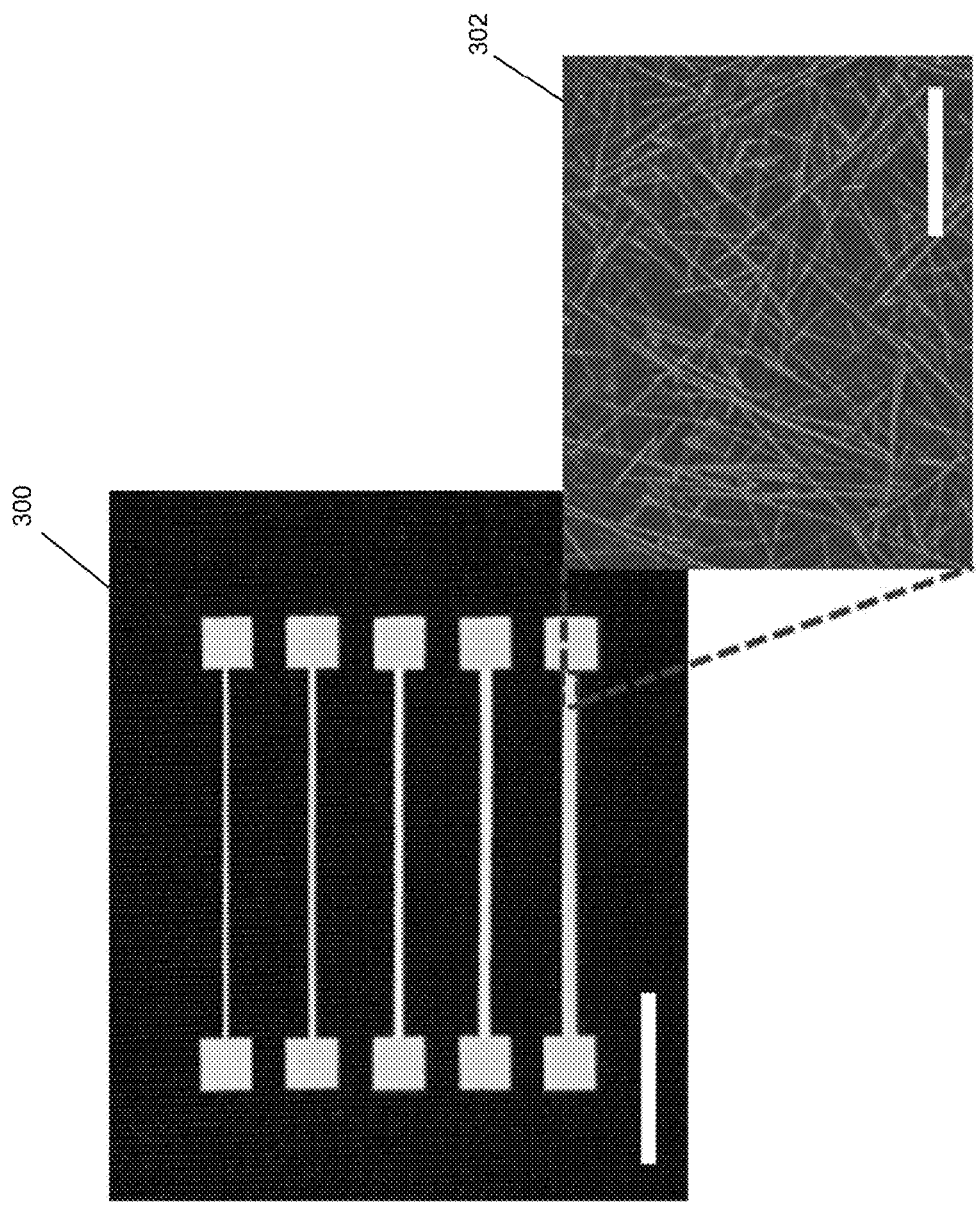
FIG. 3 depicts a photograph illustrating laminated nanocomposite patterns according to an embodiment of the subject matter described herein.
Figure 4:
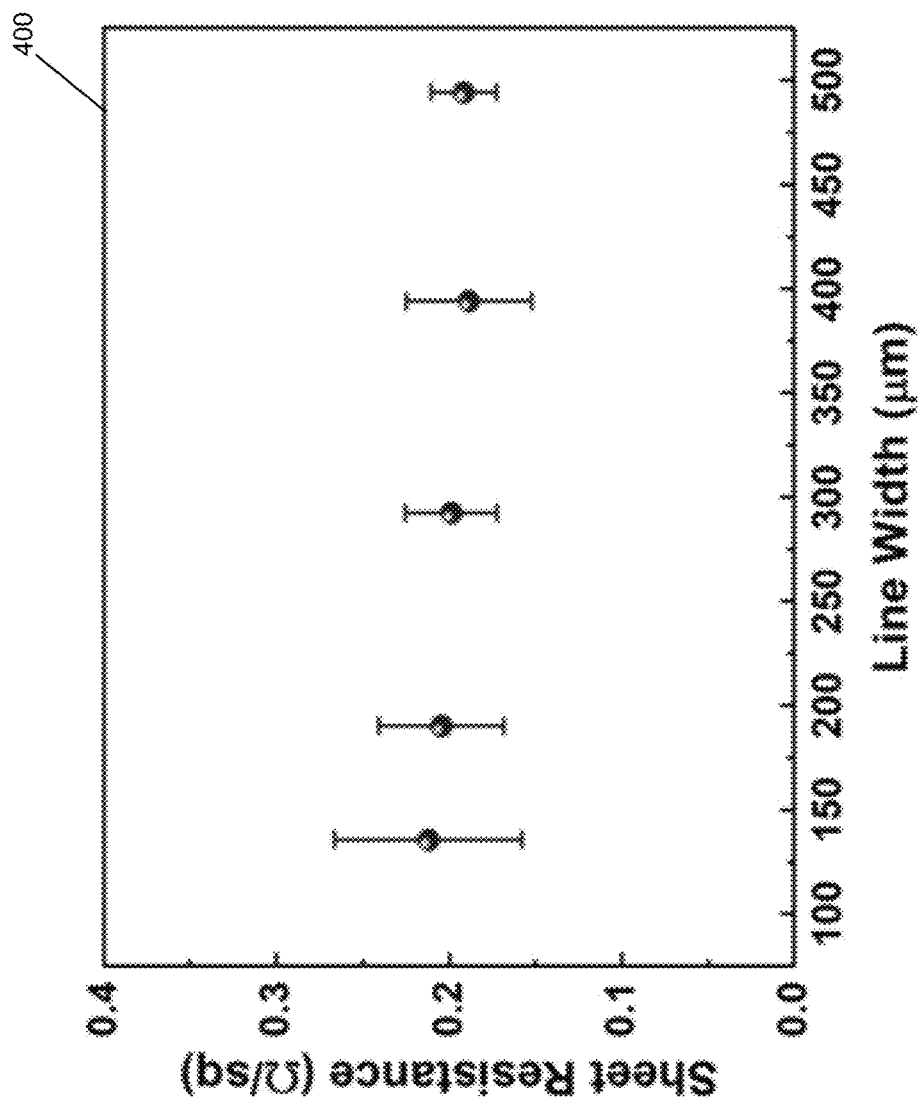
FIG. 4 illustrates an exemplary line graph depicting the sheet resistance of laminated nanostructures on a textile material with different line widths according to an embodiment of the subject matter described herein.

In FIG. 2, graph 200 displays the sheet resistances of the AgNWs coated on the glass substrate, AgNWs/TPU nanocomposites on the glass substrate, and AgNW/TPU laminated on textile materials for different AgNW densities, respectively, with the same linewidth (e.g., linewidth: 200 μm). Notably, the sheet resistance increases after the introduction of insulating TPU and slightly decreases after the heat press laminating processing. Mechanical compression and thermal annealing can reduce the contact resistance between AgNWs, leading to the enhanced conductivity after the heat press processing. Image 300 in FIG. 3 shows the patterned AgNW/TPU nanocomposites on textiles with different linewidths, ranging from 135 μm to 500 μm (e.g., laminated AgNW/TPU patterns with different linewidth with AgNW density of 0.48 mg/cm$^2$ (scale bar: 5 mm)). Inset 302 in FIG. 3 shows the top view SEM image of the AgNW/TPU pattern (scale bar: 5 μm). As can be seen from the inset SEM image 302, AgNWs can be embedded just below the surface of TPU and randomly distributed to form a percolation network. The sheet resistance may be measured to be 0.2 Ω/sq. For example, see graph 400 in FIG. 4, which shows the sheet resistance of the laminated AgNW/TPU nanocomposite on textile materials with different line widths.

Figure 5:
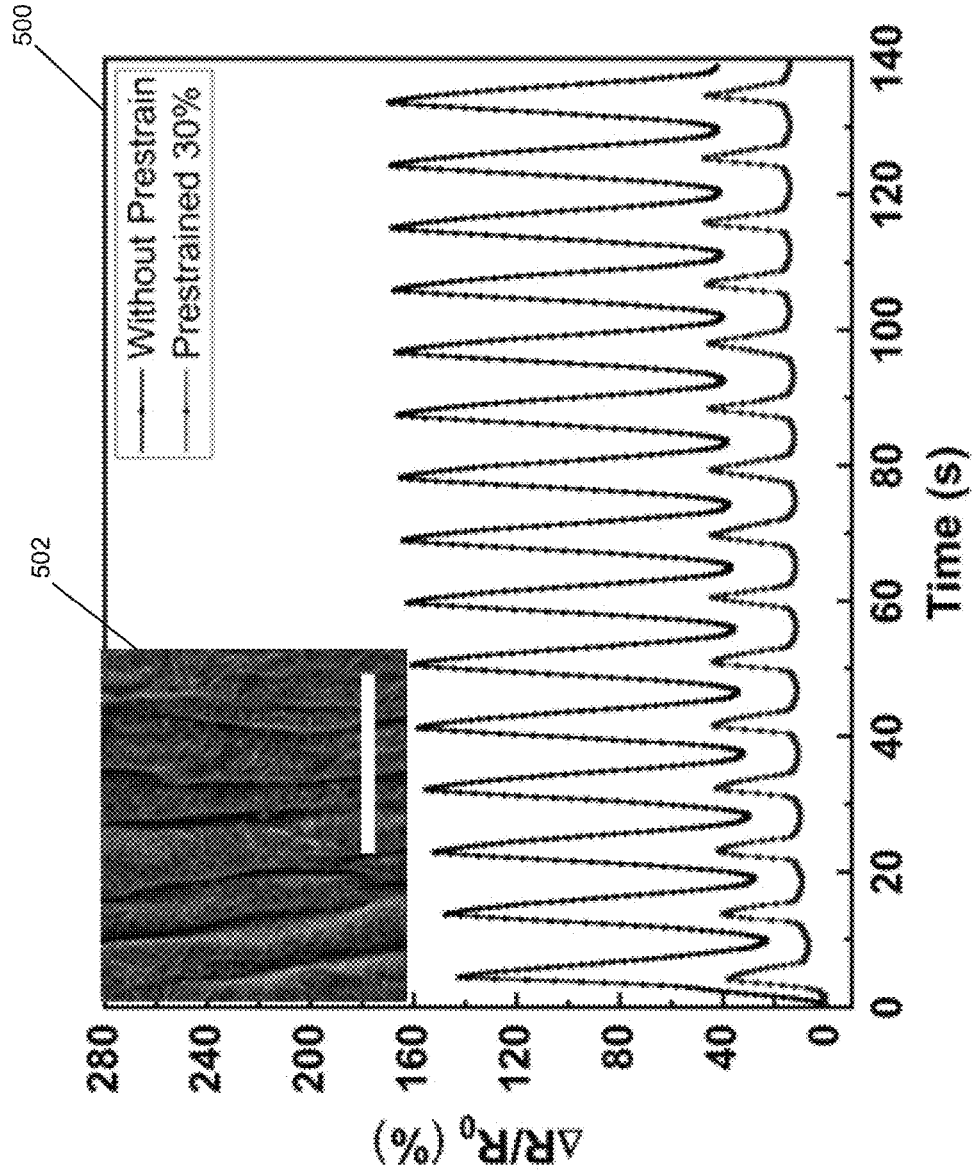
FIG. 5 illustrates an exemplary line graph depicting the resistance change of nanocomposite patterns on unstrained and pre-strained textile materials according to an embodiment of the subject matter described herein.

To test the electromechanical stability of the laminated AgNW/TPU on textile materials, the samples with different patterns were mounted onto a motorized tensile stage to apply the strain. As shown in graph 500 in FIG. 5, for a straight line pattern, the resistance increased dramatically during the first stretching/releasing cycle with a tensile strain of 50%. Notably, the resistance does not revert to the original value upon releasing the strain, mainly due to the irreversible sliding of the AgNWs in the polymer matrix. Following the approach of prestrain-release-buckling, a more stable resistance under strain can be achieved. As an example, the textile substrate can be prestrained by 30% before bonding and/or heat pressing the AgNW/TPU patterns onto the textile material. After releasing the prestrain, a buckling structure was generated in the AgNW/TPU nanocomposites (see inset 502 in graph 500). During the following stretching, the buckling structure accommodated most of the strain and relieved the strain experienced by the AgNW/TPU nanocomposites. As a result, the resistance change under strain was significantly decreased (see graph

Figure 6:
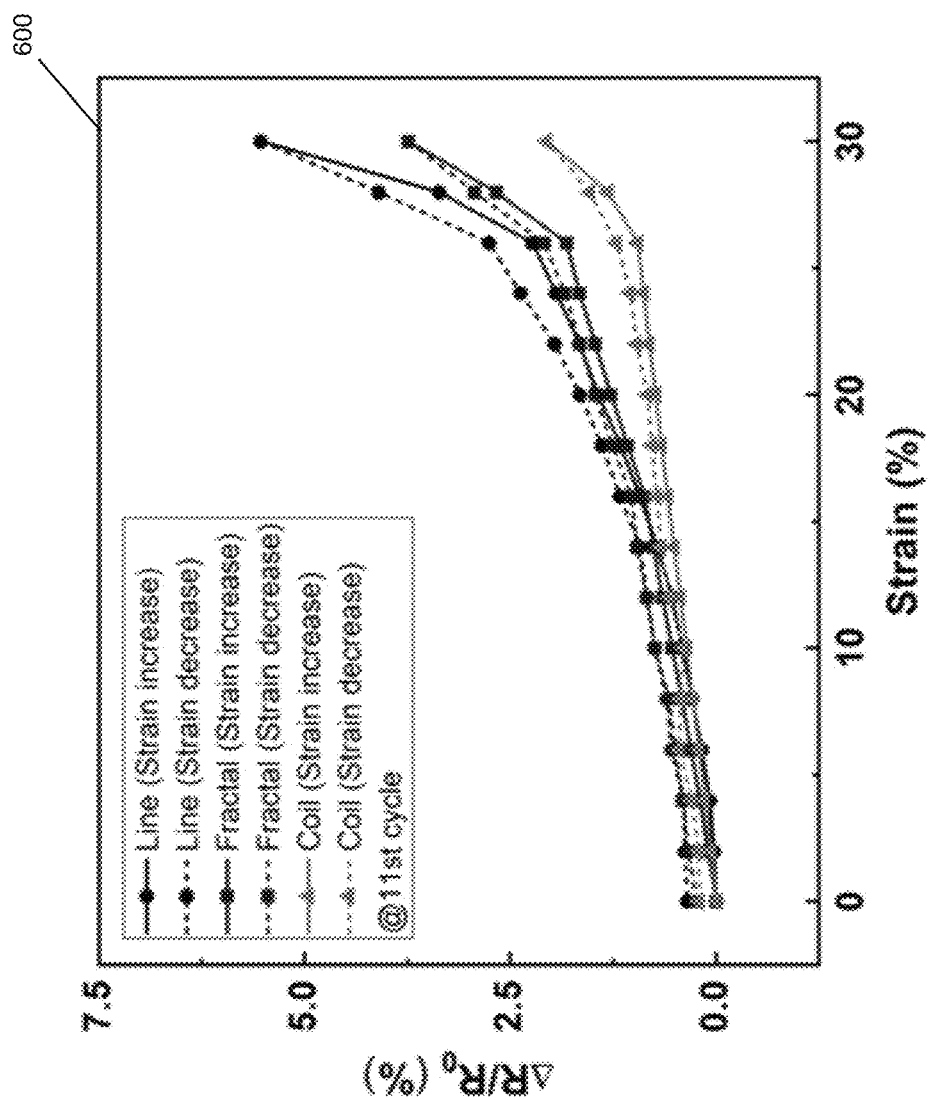
FIG. 6 illustrates an exemplary line graph depicting the resistance change of nanocomposite patterns on pre-strained textile materials for different patterns according to an embodiment of the subject matter described herein.
Figure 21:
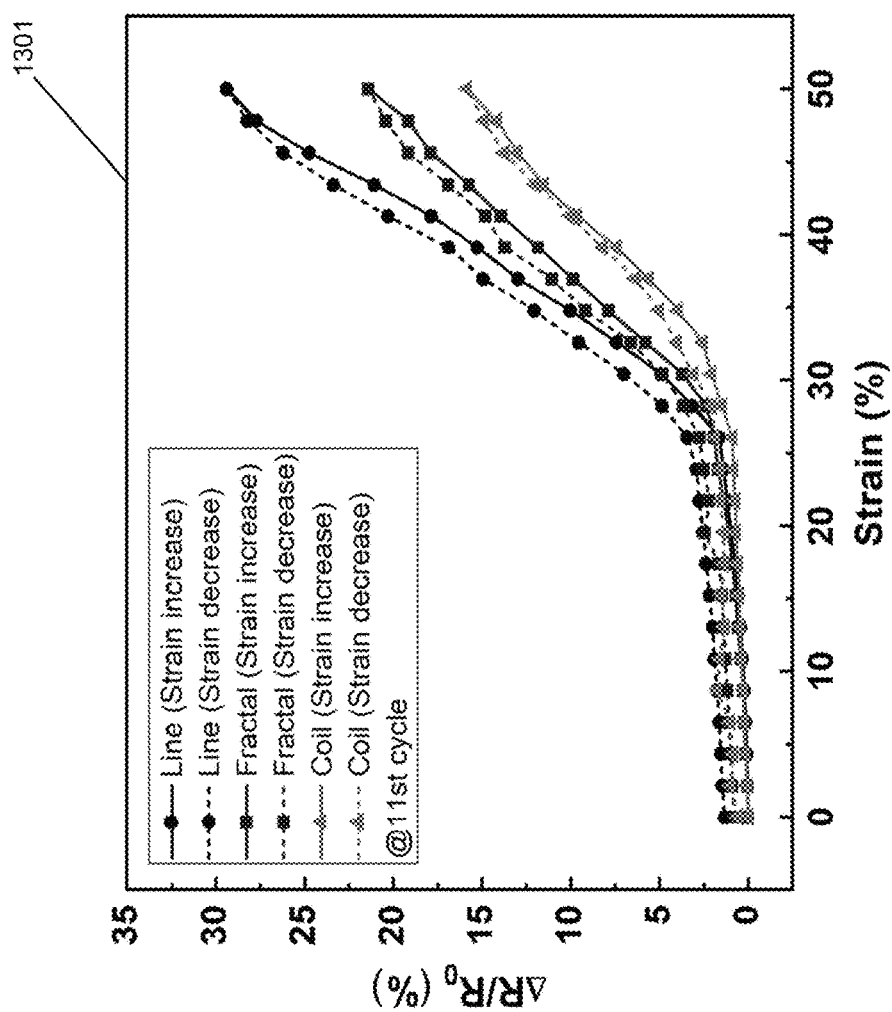
FIG. 21 depicts a graph illustrating the resistance change of nanocomposite pattern elements according to an embodiment of the subject matter described herein.

600 in FIG. 6, which shows resistance change of AgNW/ TPU patterns laminated on prestrained (30%) textiles as a function of strain (up to 30%) for different patterns. The results for 50% strain are provided in FIG. 21, which illustrates the resistance change of AgNW/TPU patterns laminated on pretrained (30%) textiles as a function of strain for different patterns. The depicted resistance changes include 29% (straight line), 21% (fractal), and 16% (coil) under 50% strain, respectively). Then two other patterns used in the integrated textile patch, e.g., Greek cross fractal patterns for dry electrodes and coil patterns for a wireless heater were transferred onto the prestrained textiles and tested. A Greek cross fractal pattern may be selected for electrophysiological electrodes, primarily due to its good stretchability and a high level of connectivity (and thus minimized resistance). This exemplary design supports robustness in the mechanical and electrical properties of the pattern. At the eleventh ($11^{th}$) cycle of stretching with 30% strain, 6%, 4% and 2% increase in the resistance was observed for the straight line, fractal, and coil patterns, respectively. The results indicated good electromechanical stability.

Figure 7:
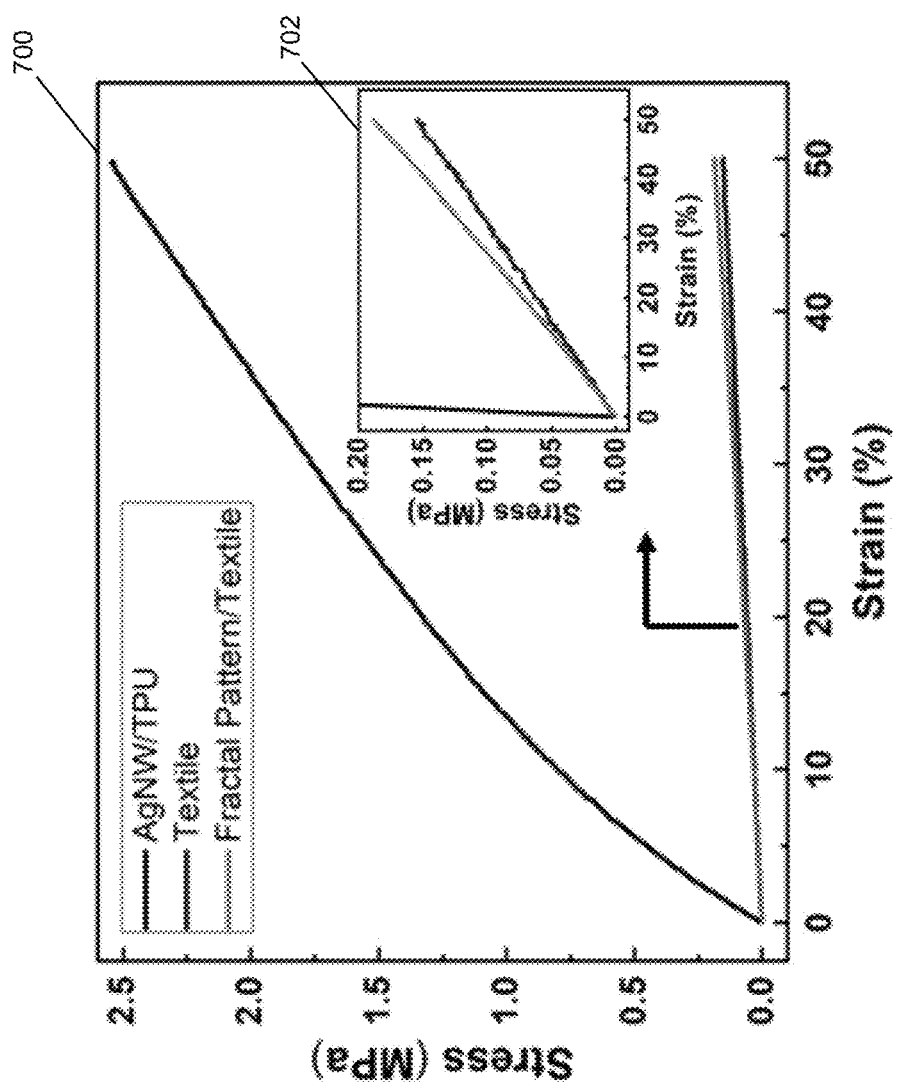
FIG. 7 illustrates an exemplary line graph depicting stress-strain curves for the textile, nanocomposite, and fractal patterns laminated on textile materials according to an embodiment of the subject matter described herein.
Figure 8:
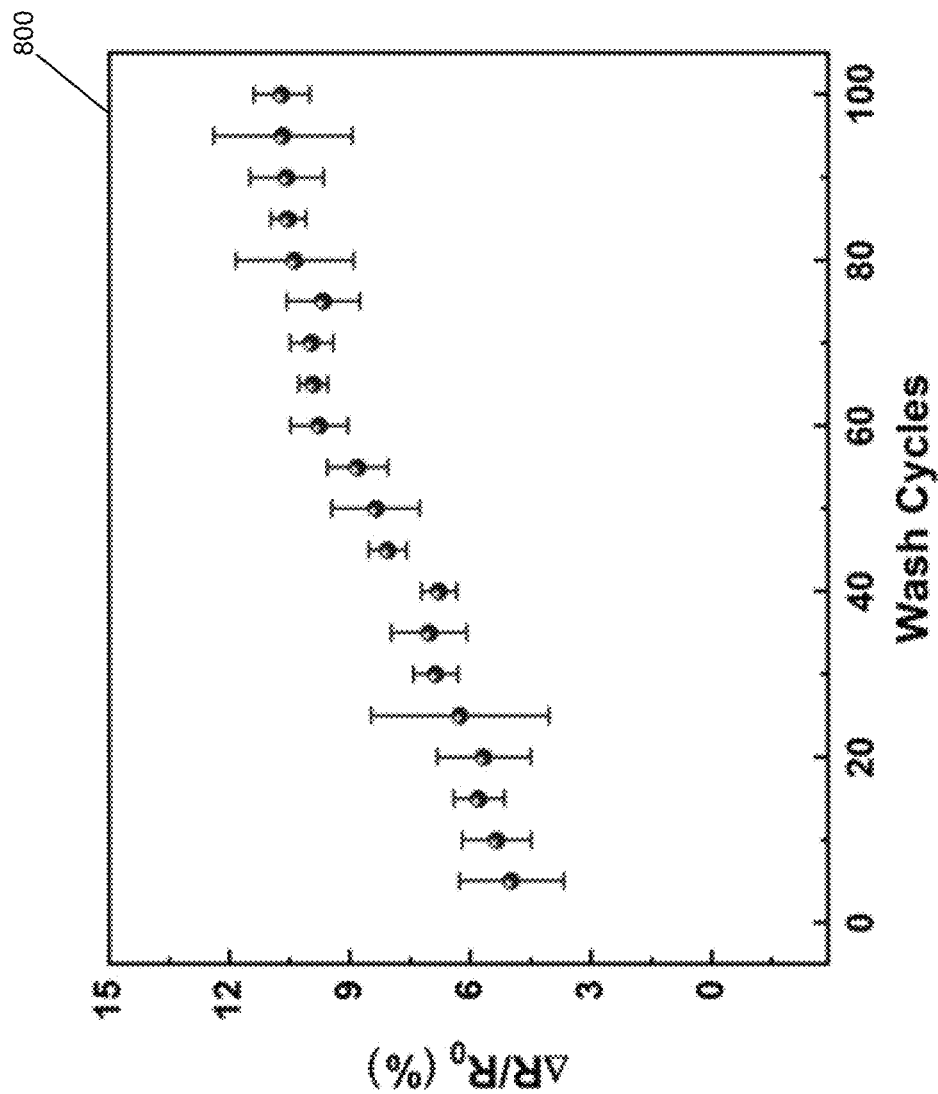
FIG. 8 illustrates an exemplary line graph that depicts the resistance change of AgNW/TPU patterns laminated on textiles as a function of washing cycles according to an embodiment of the subject matter described herein.

In some embodiments, stress-strain curves of the original textiles and textiles with AgNW/TPU patterns were measured to assess the mechanical properties of the integrated textiles (see graph 700 in FIG. 7 which shows stress-strain curves for the textile fabric, AgNW/TPU composites, and fractal patterns laminated on textiles). An inset 702 in FIG. 7 shows an enlarged view of the stress-strain curve. Due to the excellent compliance of the nanocomposites and the introduction of stretchable structures (e.g., wavy structure and fractal patterns), nearly no change in mechanical properties are observed after laminating AgNW/TPU patterns onto the textile materials. Moreover, the washability of the textile integrated AgNW/TPU fractal patterns were tested according to the standard ISO 6330:2000. In some example instances, E-textile samples (e.g., contained in a laundry bag) were placed into the washing machine together with ballast to reach a 2 kilogram standard load. The samples were drip dried at room temperature after each washing process. Graph 800 in FIG. 8 summarizes the resistance change as a function of the washing cycle. The resistance change increased around 10% after 100 washing cycles, which is likely due to the combined effects of mechanical distortion, thermal stress, and moisture. The increase in resistance during washing is lower than that for screen printed Ag/AgCl inks on TPU, Cu-PET yarns, sewn conductive threads, PEDOT:PSS coated knitted fabrics, and comparable to that of liquid metal enabled elastomeric microfibers. The encapsulation of the nanostructure network by the thermoplastic elastomer (e.g., TPU) is conducive to the rigors of the washing process.

Figure 9:
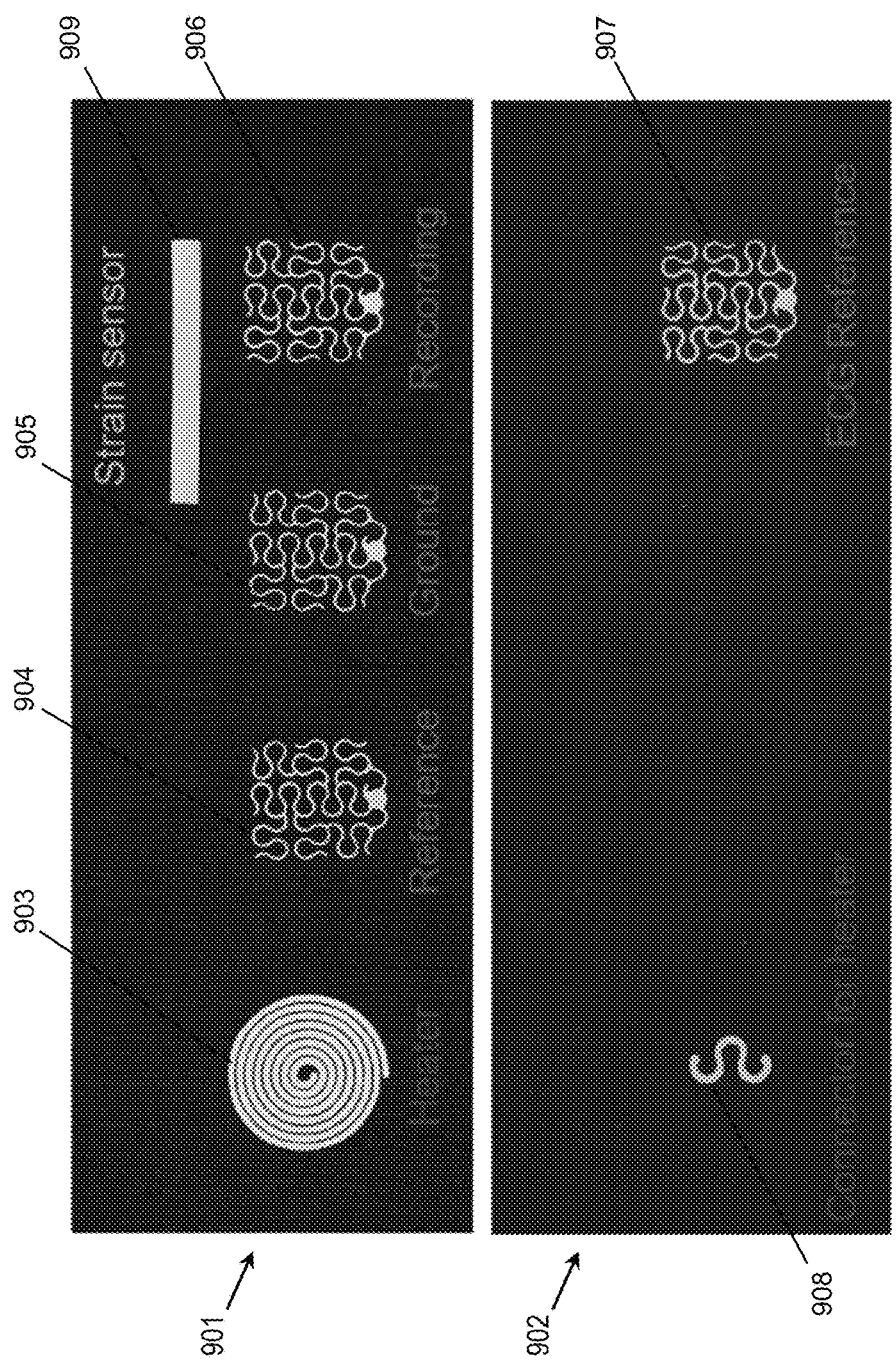
FIG. 9 depicts the front and back views of an exemplary integrated textile patch according to an embodiment of the subject matter described herein.
Figure 10:
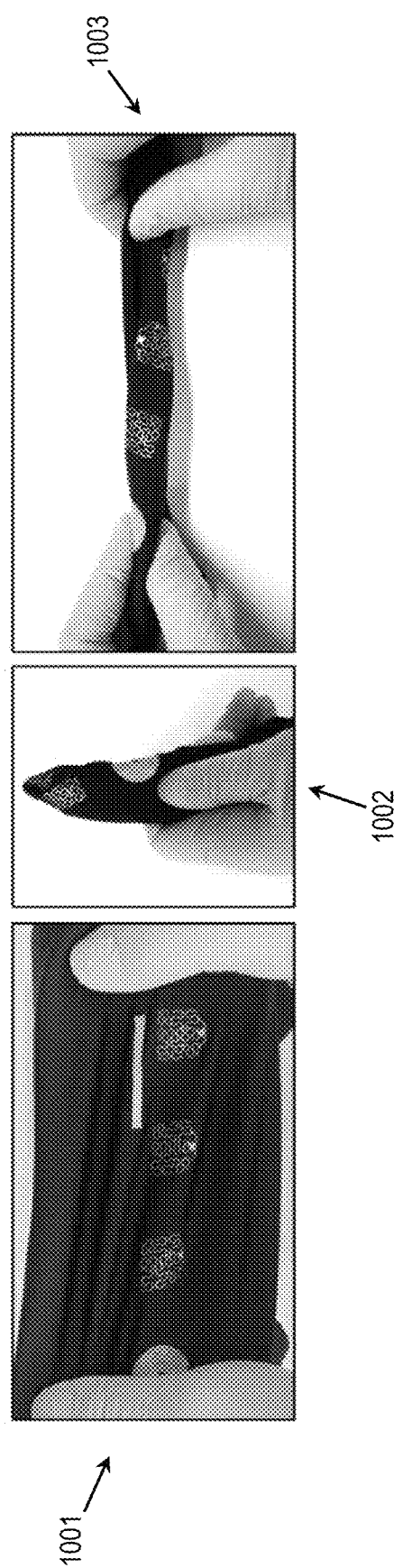
FIG. 10 depicts an exemplary integrated textile patch that is being stretched, folded, and twisted according to an embodiment of the subject matter described herein.

To illustrate the potential applications of the E-textiles, one embodiment may include three devices being integrated into a textile patch (see photographs 901-902 in FIG. 9), demonstrating an example sports application. Notably, FIG. 9 illustrates an integrated textile patch comprising of four dry electrodes 904-907 (e.g., three electrodes 904-906 are in the front), a capacitive strain sensor 909, and a wireless heater 903 (and a connector 908 for heater 903 on the opposite side) for sports applications. Photograph 901 is a picture of the front side of the patch and photograph 902 is a picture of the back side of the patch). The patch is stretchable, foldable and twistable (see photographs 1001-1003 in FIG. 10), as expected during sporting activities. Three dry electrodes with Greek cross fractal patterns were fabricated for electrophysiological applications. These electrodes can be used to record both heart activities (e.g., electrocardiography (ECG)) and muscle activities (e.g., electromyography (EMG)), which are of great interest for tracking sports performance. Heart rate can be readily derived from the R-R interval of the ECG signal. Beyond heart rate, ECG recording represents one of the most commonly used tools to diagnose and manage cardiovascular diseases, which is the leading cause of death. EMG sensing plays an important role in evaluating the health of muscle tissues and nerves, and in diagnosing neuromuscular disorders and motor neuron dysfunctions. It is worth noting that electrodes 904-907 demonstrated here are dry, eliminating the conductive gel that is commonly used in commercial disposable electrodes. The dry electrodes address the major challenges faced by pre-gelled electrodes for long-term applications—signal quality degradation caused by dehydration of the gel with time, potential skin irritation evoked by the gel, and the inconvenience associated with repeatedly reapplication of new gel.

Figure 22:
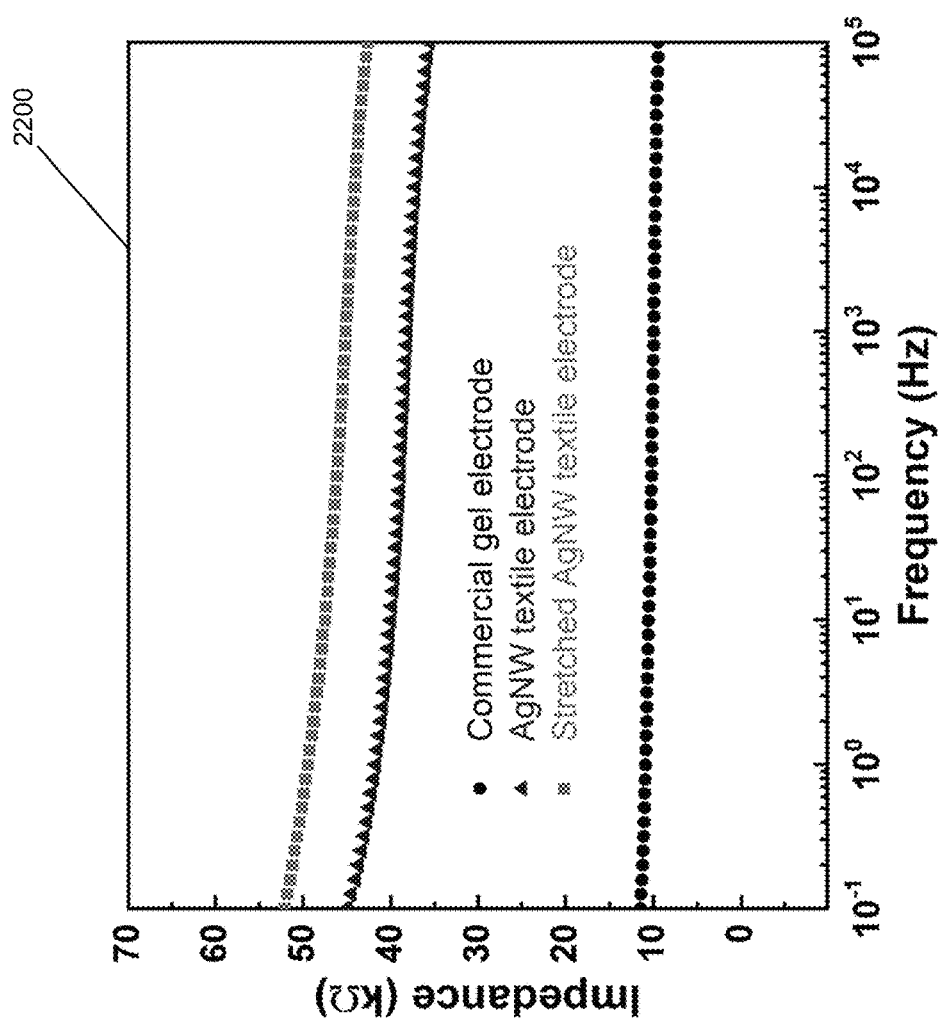
FIG. 22 depicts a graph illustrating the electrode-skin impedance for different electrodes according to an embodiment of the subject matter described herein.

The electrode-skin impedance of the commercial gel electrodes and the fabricated dry textile electrodes were measured by placing two electrodes on the forearm with the electrodes 30 mm apart (center-to-center). Without the gel, the dry textile electrodes exhibited only slightly higher electrode-skin impedance than commercial gel electrodes, owing to the excellent compliance and very high conductivity. For example, see graph 2200 in FIG. 22 which shows electrode-skin impedance for commercial gel electrodes, dry AgNW based textile electrodes, and stretched AgNW based textile electrodes. Upon the application of 50% strain, the electrode-skin impedance of the dry electrodes is marginally increased.

Figure 11A:
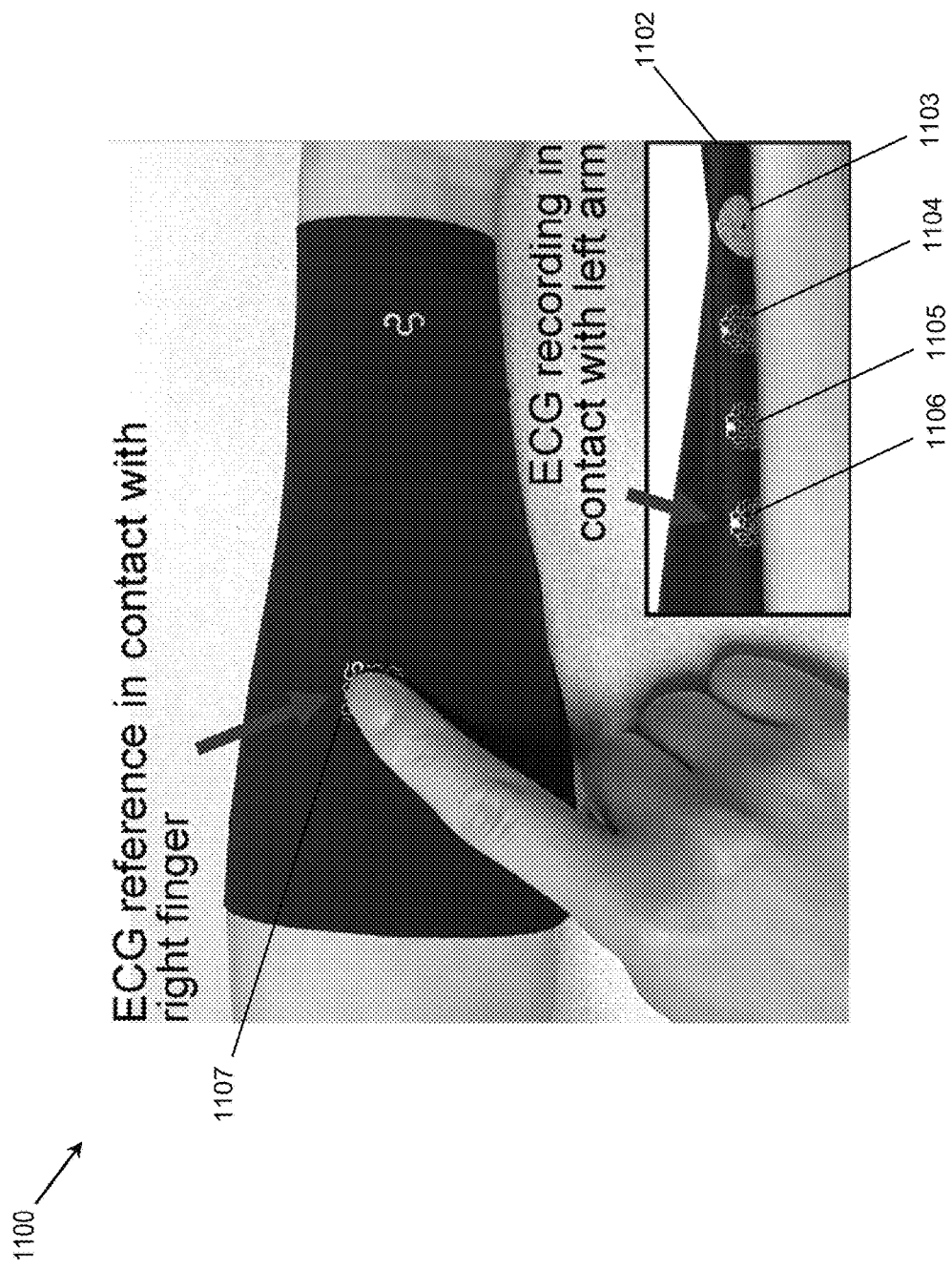
FIGS. 11A and 11B depict an integrated textile sports sleeve product configured with electrocardiography (ECG) electrodes and electromyography (EMG) electrodes according to an embodiment of these subject matter described herein.
Figure 11B:
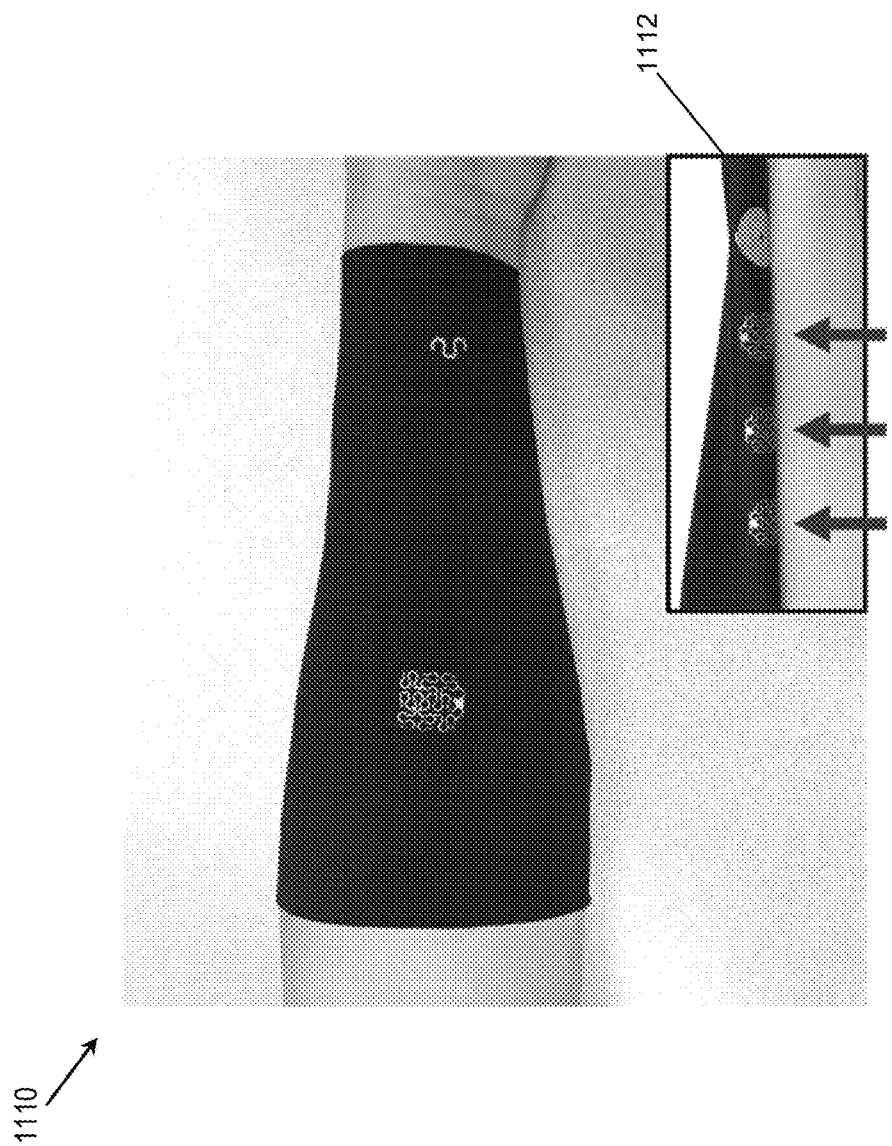
Figure 12:
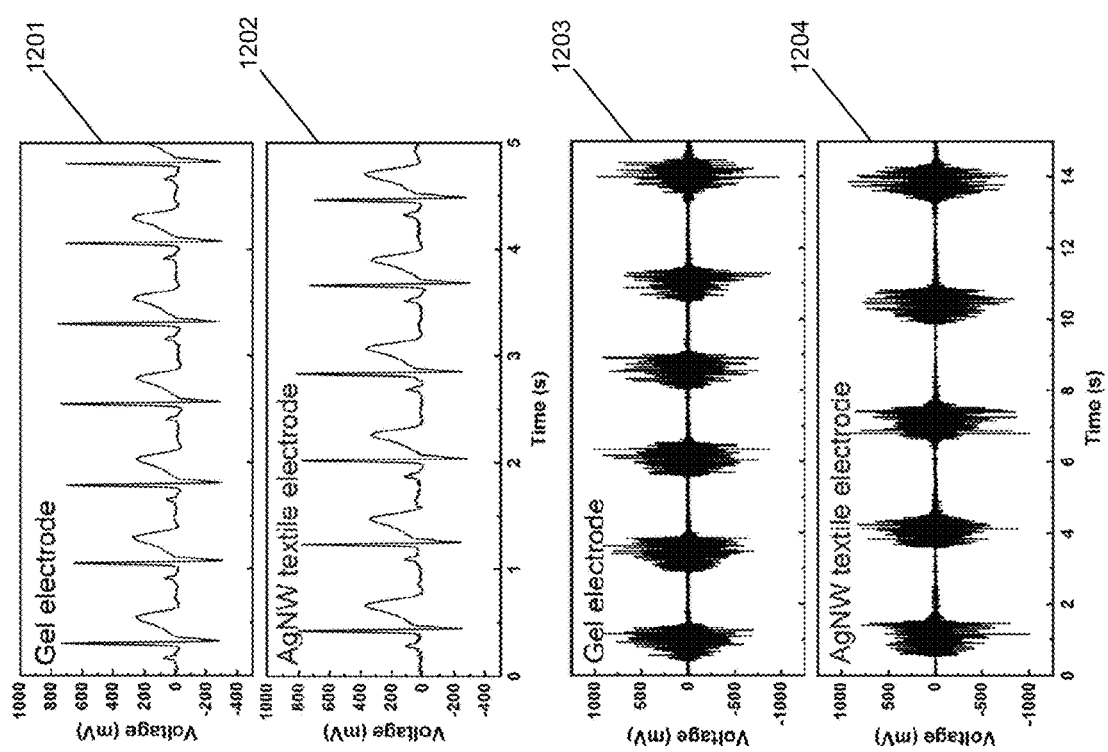
FIG. 12 illustrates a plurality of graphs depicting the comparison of electrocardiography (ECG) signals and electromyography (EMG) signals utilizing dry and gel electrodes according to an embodiment of the subject matter described herein.
Figure 23:
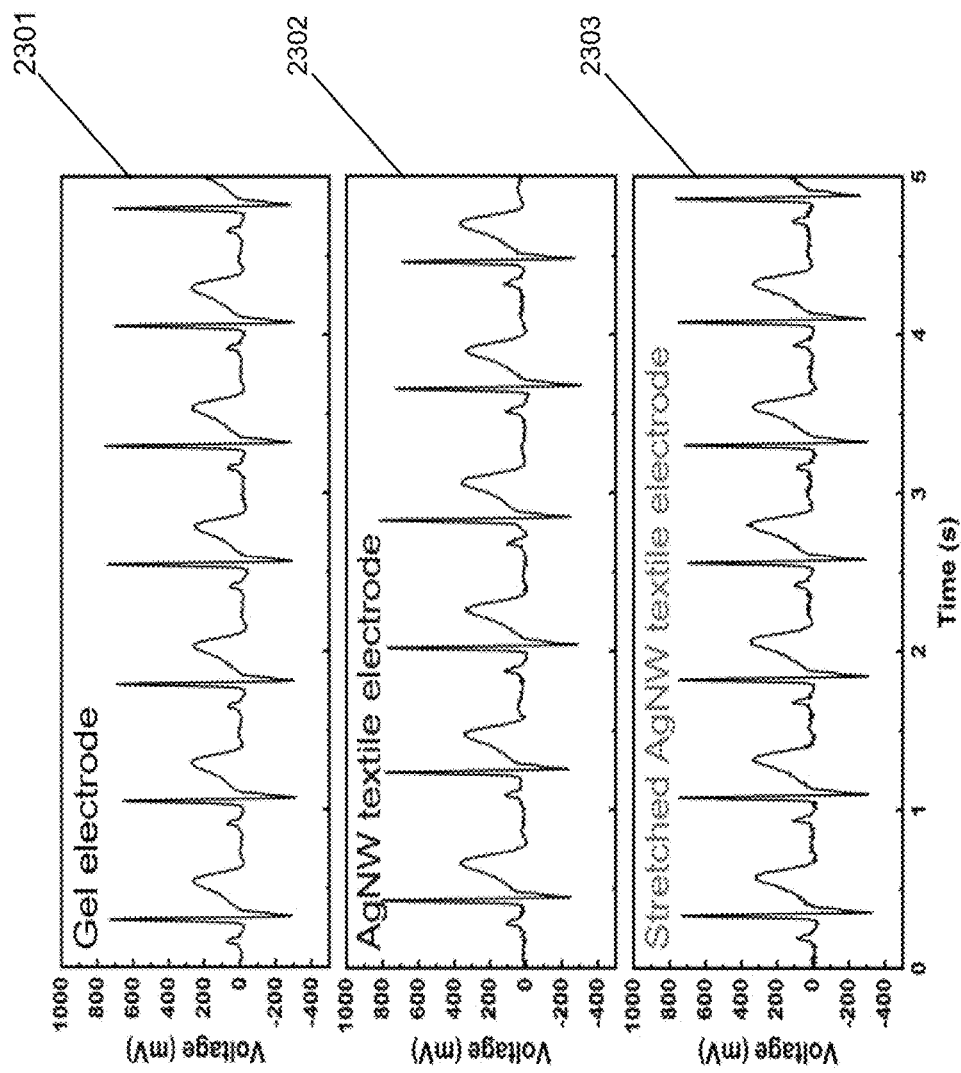
FIG. 23 depicts a graph illustrating the comparison of ECG measurements for different electrodes according to an embodiment of the subject matter described herein.
Figure 24:
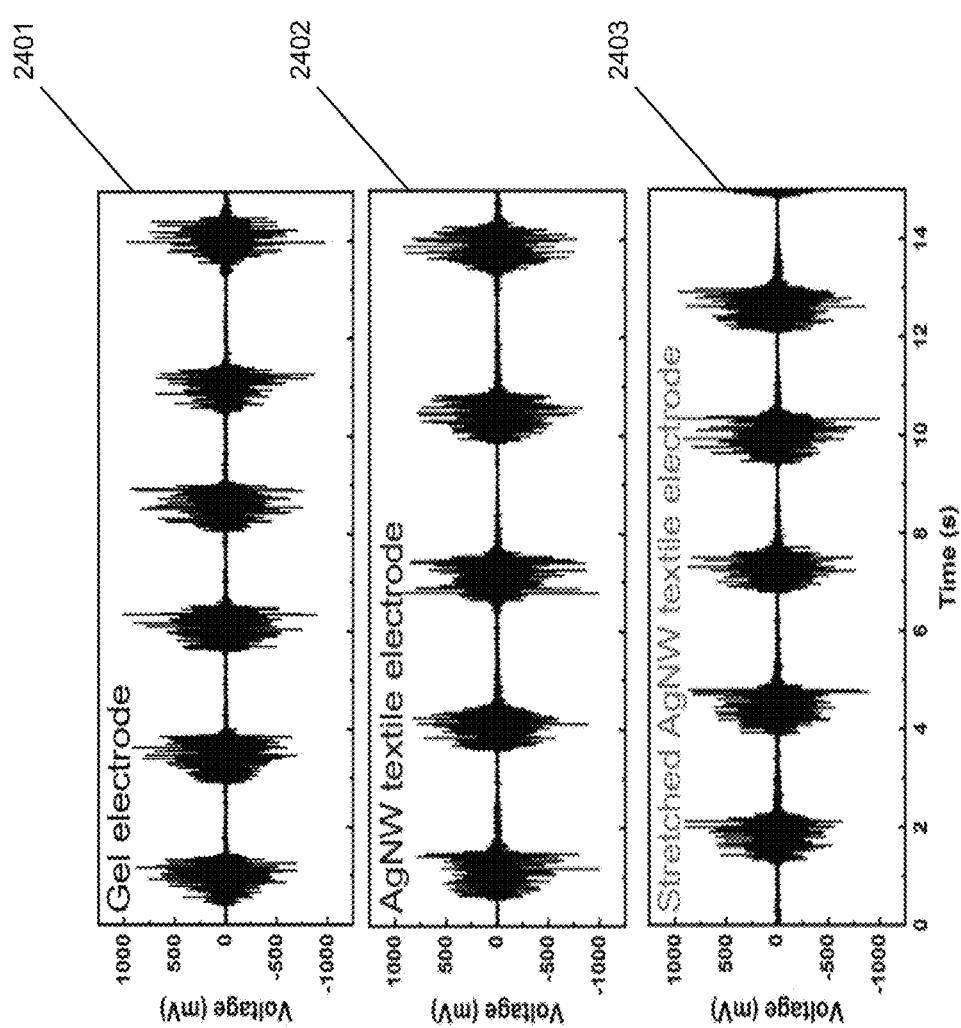
FIG. 24 depicts a graph illustrating the comparison of EMG measurements for different electrodes according to an embodiment of the subject matter described herein.

In some embodiments, ECG signals can be captured using the right electrode (e.g., ECG recording electrode) as the recording electrode 1106 and the back electrode 1107 as the reference electrode (e.g., ECG reference electrode) as shown in photograph 1100 and inset 1102 of FIG. 11A. Specifically, FIG. 11A depicts a photograph 1100 (and inset 1102) showing an example sports sleeve configured to conduct ECG measurements. The recording electrode 1106 may be in contact with the left forearm and the reference electrode 1107 may be touched by a right index finger. Inset 1102 further shows heater 1103 and electrodes 1104-1106 in contact with the left forearm of the subject. FIG. 11B depicts a photograph 1110 (and inset 1112) showing an example sports sleeve configuration of EMG measurements with the left electrode 1106 as the recording electrode, right electrode 1104 as the reference, and middle electrode 1105 as the ground. EMG electrodes are positioned on the inner side of the sports sleeve to make direct contact with skin. The gathered signals from the commercial gel electrodes and dry textile electrodes are comparable, and no apparent signal degradation is observed for stretched dry textile electrodes at 50% strain (see graphs 1201-1202 in FIG. 12 showing a comparison of ECG signals between commercial gel electrodes and dry AgNW based textile electrodes). Similarly, graphs 2301-2303 in FIG. 23 depicts a comparison of ECG measurements of (a) commercial gel electrodes (graph 2301), (b) dry AgNW based textile electrodes (graph 2302), and (c) stretched AgNW based textile electrodes at 50% strain (graph 2303). The P wave, QRS complex, and T wave can all be clearly identified on the three curves. For the surface EMG measurement, the recording (right), reference (left) and ground (middle) electrodes were placed on the forearm, parallel to the muscle fiber direction. EMG signals corresponding to the muscle contraction during the clenching of a fist can be clearly detected (see photograph 1100 in FIG. 11 showing the configuration of EMG measurements via an equipped sports sleeve). Comparable EMG signals were obtained from the commercial gel electrodes and from the unstretched (non-strained) and stretched (strained) dry textile electrode, respectively (see graphs 1203-1204 in FIG. 12 showing a comparison of EMG signals between commercial gel electrodes and dry AgNW based textile electrodes). Similarly, graphs 2401-2403 in FIG. 24 show a comparison of EMG measurements for (a) commercial gel electrodes (graph 2401), (b) dry AgNW based textile electrodes (graph 2402) and (c) stretched AgNW based textile electrodes at 50% strain (graph 2403). These results indicate that AgNW-based textile electrodes, in a dry and wearable form, can be employed to measure high quality ECG and EMG signals.

Figure 13:
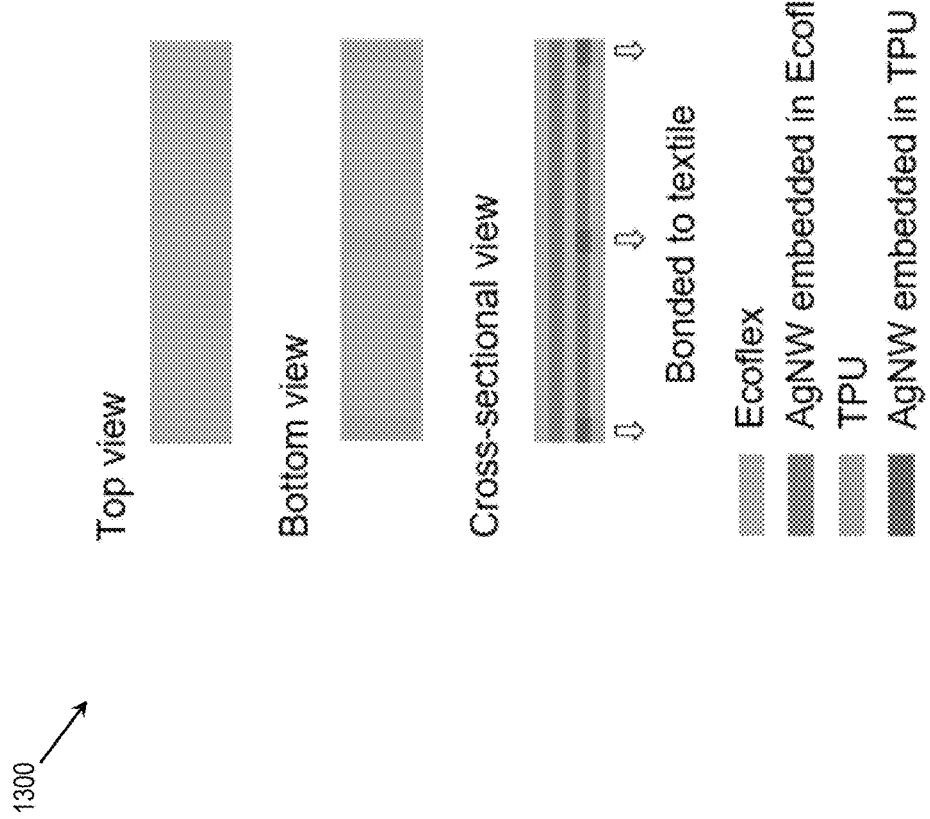
FIG. 13 illustrates an exemplary structure schematic of a textile integrated capacitive strain sensor device according to an embodiment of the subject matter described herein.
Figure 16:
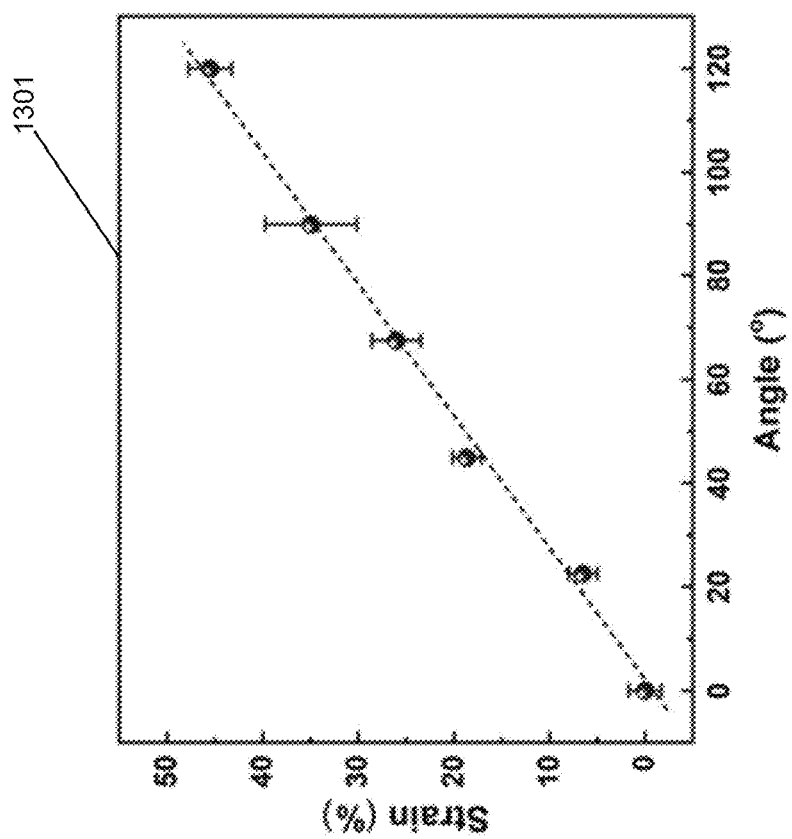
FIG. 16 illustrates a calibration curve for a textile integrated capacitive strain sensor device and a graph illustrating the strain associated with different elbow bending angles according to an embodiment of the subject matter described herein.
Figure 16:
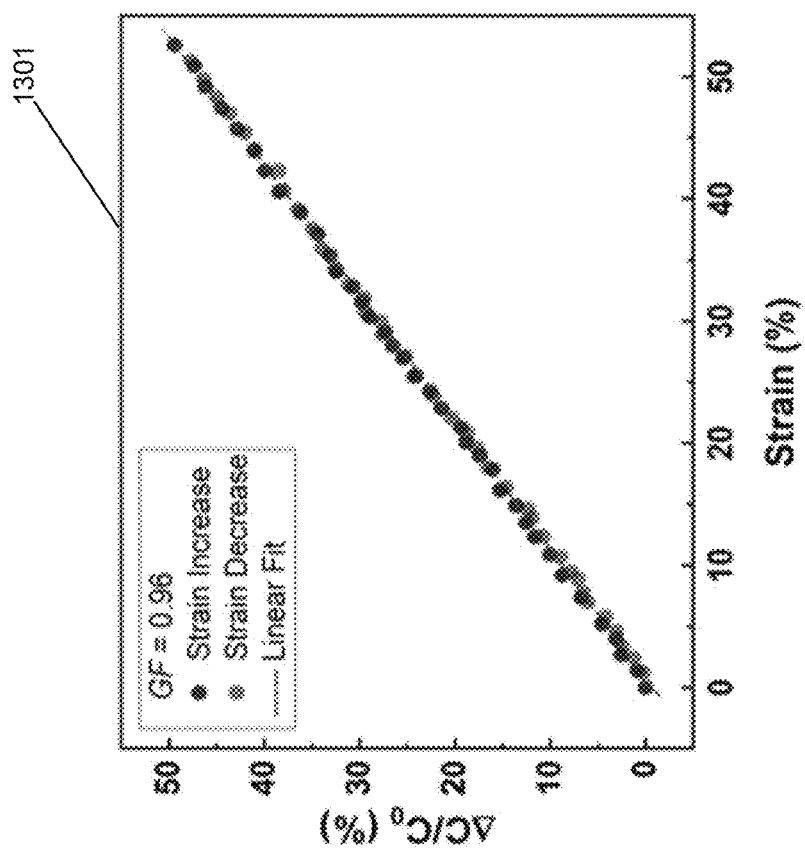

In some embodiments, the laminated AgNW/TPU nanocomposites can also be combined with other soft textile materials to realize textile-based wearable applications. As an example, a capacitive strain sensor using AgNW/TPU and AgNW/Ecoflex nanocomposites can be incorporated into an E-textile patch to track the body movements. As shown in the schematics in FIG. 13 (see diagram 1300 showing a schematic structure of a textile integrated capacitive strain sensor), the top electrode of the stretchable capacitor was made by embedding AgNWs just below the surface of a highly compliant elastomer (e.g., Smooth-on Ecoflex 0030). For the bottom electrode, AgNWs were firstly embedded in TPU for selected areas. A layer of liquid Ecoflex was then coated onto the remaining AgNW areas while exposing enough TPU area to provide a strong bonding to the textile. The structure ensures a sufficiently low Young's modulus of the sensor so as not to disrupt the natural body movements. The top and bottom electrodes were then sandwiched by a thin layer of Ecoflex as the dielectric with the AgNW side face to face. The elongation of the stretchable capacitor leads to an increase in the capacitance, as shown in the calibration curves in graph 1601 in FIG. 16 (i.e., calibration curve for the textile integrated capacitive strain sensor during strain increase and decrease). The gauge factor of the capacitive strain sensor, defined as the change in the capacitance (C) divided by the applied tensile strain ($\varepsilon$), GF=($\Delta$C/ $C_0$)$\varepsilon$, was calculated to be 0.96 over a strain range up to 50%. The correlation between the capacitance change and the strain is linear and reversible. The strain sensing range is sufficient for the strain level associated with typical human motions.

Figure 14:
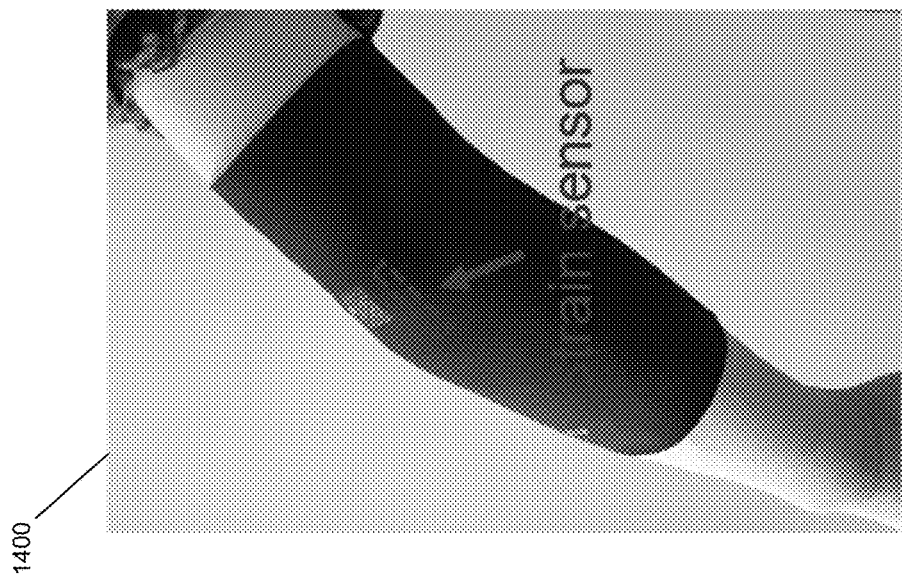
FIG. 14 illustrates the placement of a textile patch within a textile integrated sports sleeve used for monitoring elbow bending tracking according to an embodiment of the subject matter described herein.
Figure 15:
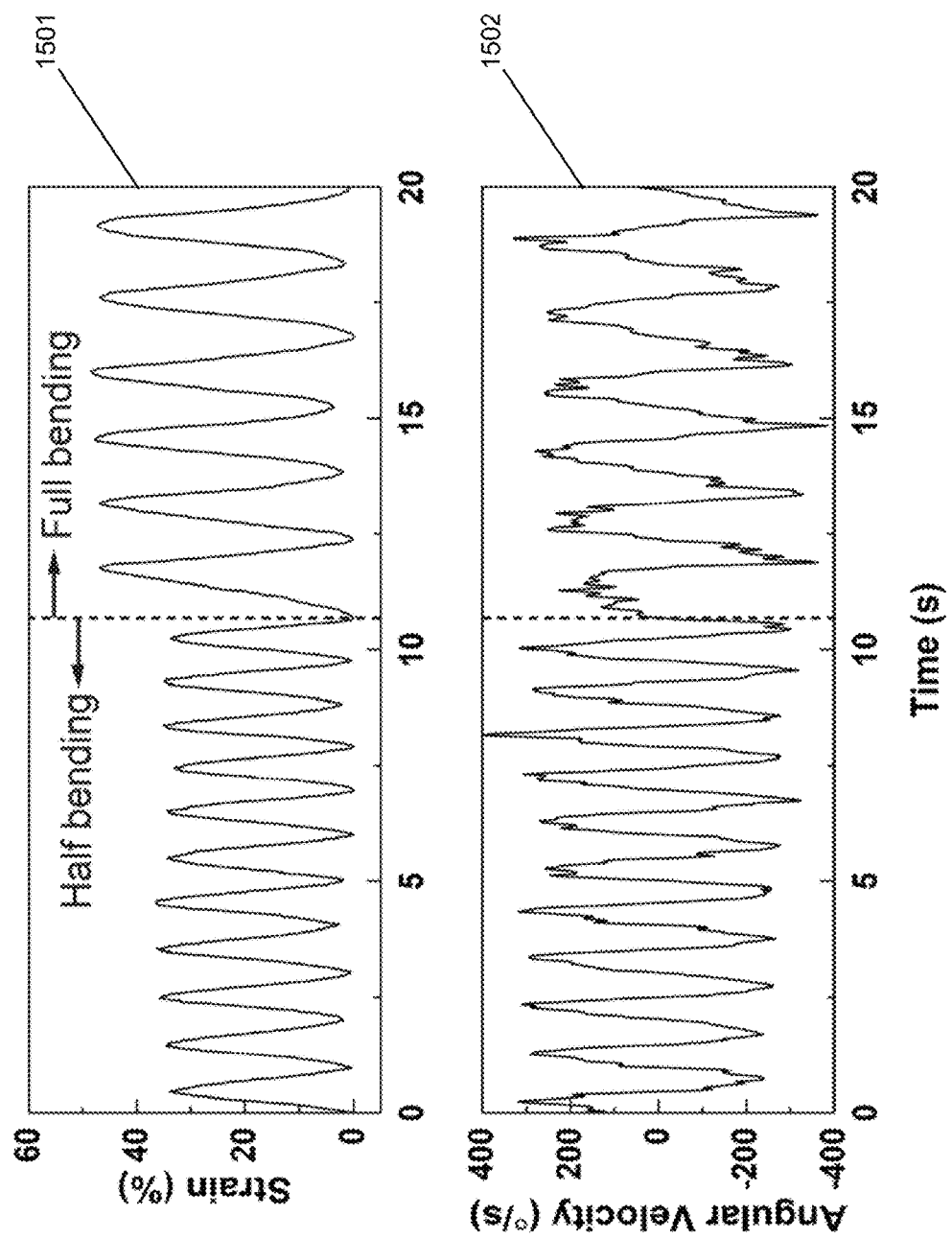
FIG. 15 illustrates a plurality of graphs depicting strain and angular velocity as a function of time during fast and slow elbow bending according to an embodiment of the subject matter described herein.
Figure 17:
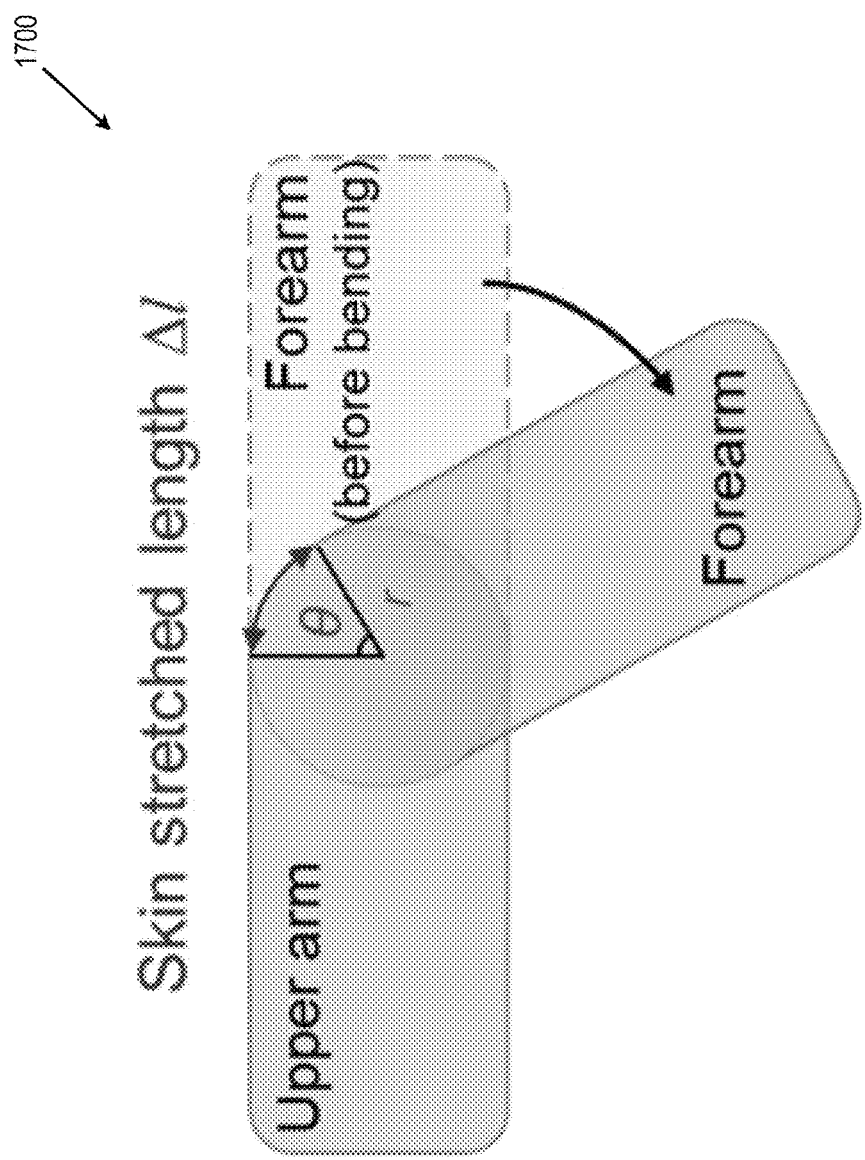
FIG. 17 illustrates a simplified model for elbow bending according to an embodiment of the subject matter described herein.

The strain sensor was mounted onto the elbow (see photograph 1400 in FIG. 14, which is a picture showing the placement of the textile patch for elbow bending tracking) to monitor the elbow bending at different bending speeds (see graphs 1501-1502 in FIG. 15, which shows strain and angular velocity as a function of time during fast and slow elbow bending). Bending angle is a more straightforward parameter to be used by athletes and trainers. Notably, the measured strain from the strain sensor is linearly proportional to the bending angle of the elbow (see graph 1602 in FIG. 16, which shows the strain associated with different elbow bending angle). This can be explained by assuming the elbow joint as a hinge-type joint, as shown schematically in diagram 1700 in FIG. 17 (which shows a simplified model for elbow bending). The change in stretched skin length along the bending direction can be approximated as $\Delta l = r\theta$, where r is the radius of the joint and $\theta$ is the bending angle. The strain experienced by the skin during elbow bending is thus $\varepsilon = \Delta l/l_0 = r\theta/l_0$, where $l_0$ is the initial length of the skin. Therefore, the strain measured by the strain sensor can be expected to be proportional to the bending angle. By converting the strain to bending angle and taking the derivative, the angular velocity associated with the elbow bending can be calculated. In this example, it was shown that from the wearable textile integrated strain sensors, important motion parameters including bending angle, strain, and angular velocity can all be obtained in real time. Such quantitative data provide valuable information to quantitatively evaluate athletic performances, improve postures, prevent injuries, and facilitate rehabilitation.

Figure 18:
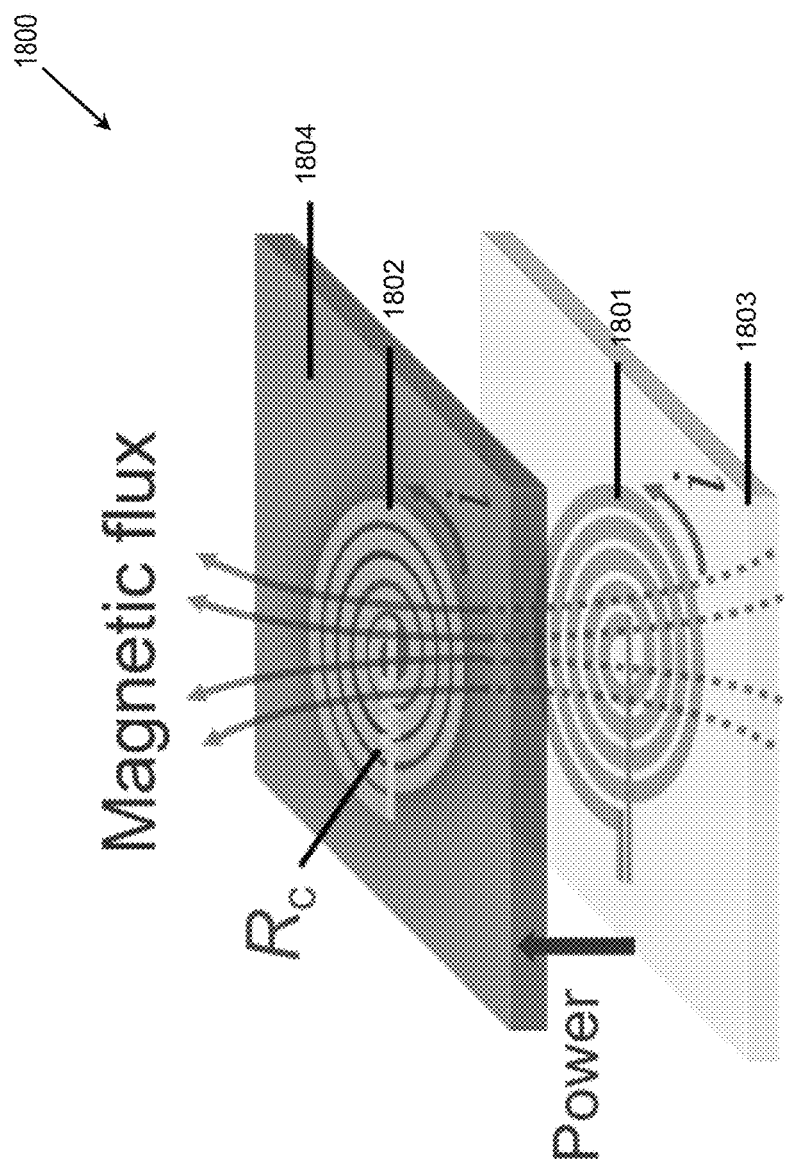
FIG. 18 illustrates an exemplary textile integrated wireless heater device according to an embodiment of the subject matter described herein.

Thermotherapy or heat therapy is widely used during rehabilitation to relieve pain and facilitate healing of sport injuries. It can take various forms, including heat pack, hot water bottle, hot shower, whirlpool bath, steam bath, sauna, and others. Heat can alleviate pain, increase blood flow, relieve muscle spasms, decrease joint stiffness, and reduce inflammation.[1] The disclosed subject matter integrates a wireless heater with the textiles to enable thermotherapy in a wireless and wearable manner. The wireless heating mechanism is similar to wireless charging. Both of them rely on inductive wireless energy transfer. Wireless charging uses a receiver inductor with an extreme low resistance to minimize the energy loss in the inductor and thus the transmitted energy can be used to charge a device. Wireless heating includes a resistive receiver inductor that converts the transmitted electrical energy into heat. As schematically illustrated in diagram 1800 of FIG. 18 (which shows a diagram of the mechanism for wireless heating), during wireless heating, alternating current in the transmitter coil 1801 (e.g., housed in the charger element 1803) generates an oscillating magnetic field, which induces an AC current in the receiver coil 1802 (e.g., the heater coil). Due to the resistive nature ($R_c$) of the receiver coil 1802, the current flowing within coil 1802 produces heat through joule heating.

Figure 19:
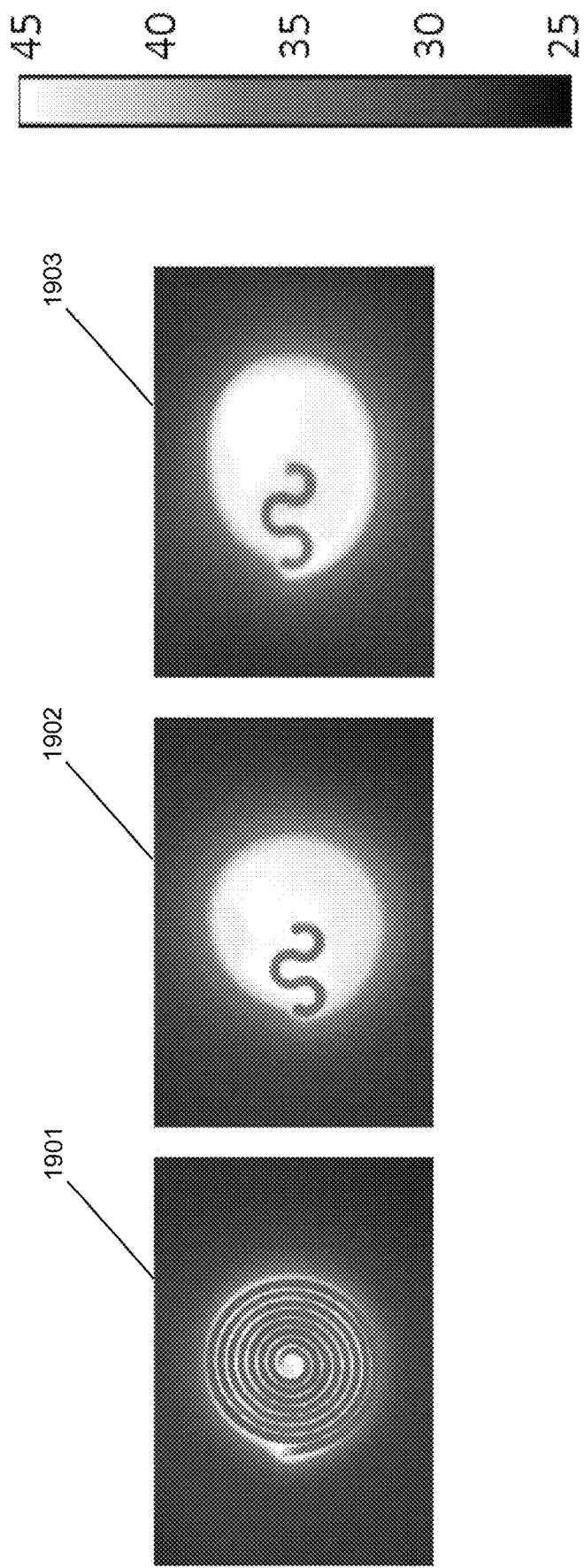
FIG. 19 illustrates infrared images depicting the temperature distribution of different sides of a heater device according to an embodiment of the subject matter described herein.
Figure 20:
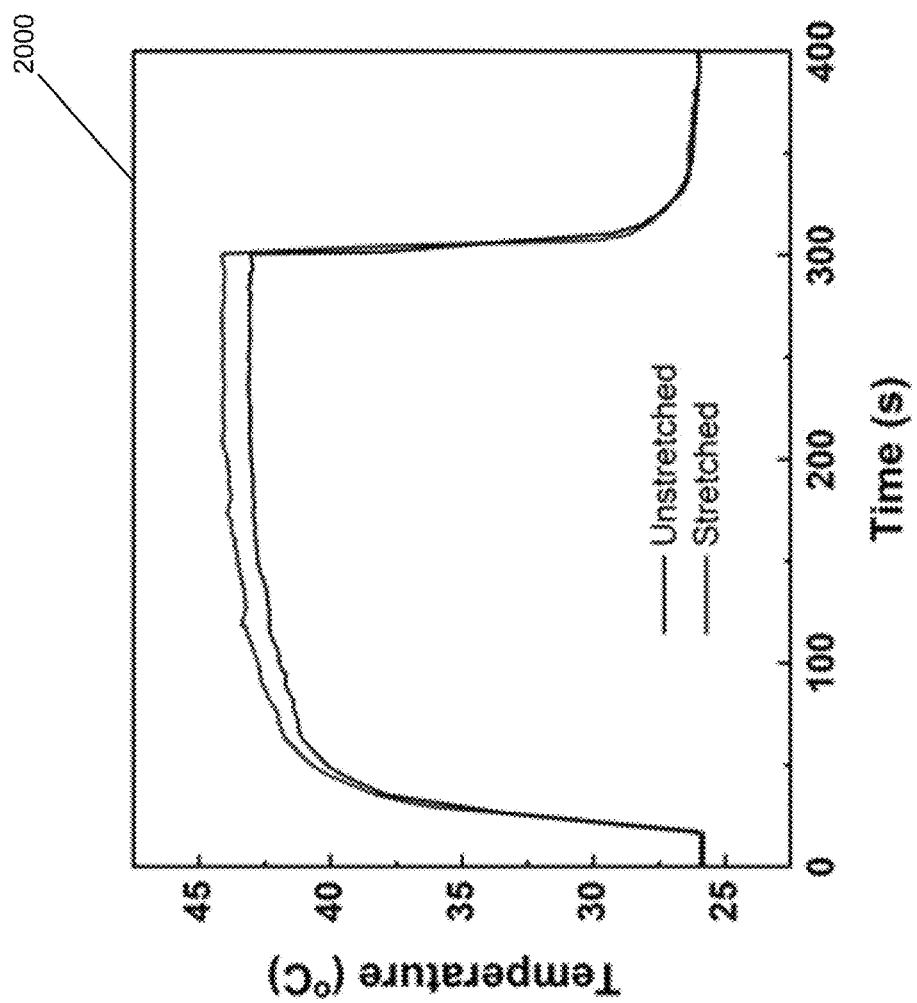
FIG. 20 illustrates time dependent temperature profiles for the unstretched heater device and the stretched heater device according to an embodiment of the subject matter described herein.

The wireless heater can be powered by any commercial Qi standard wireless charger. The heater is designed to achieve the recommended temperature range for thermotherapy (between 40° C. to 45° C.). Photographs 1901-1903 in FIG. 19 show the temperature distribution of the heater, taken using an infrared (IR) camera, after being powered for one minute (e.g., IR images showing the temperature distribution of the front of the heater). Since silver has a very low emissivity, the AgNW/TPU heater appears "cold" in the thermal image. The true temperature is better reflected in the textile material. For this reason, the IR images were mostly taken from the backside of the heater. Photographs 1901-1903 in FIG. 19 (e.g., photographs 1902 and 1903 depicting the backside of the heater and the backside of the stretched (30%) heater) compare the temporal profile and the temperature distribution of the heater without strain and with 30% uniaxial strain, respectively. Under stretching, the temperature is slightly higher than that of the unstrained state, which can be attributed to the enlarged area of the heater coil (e.g., receiver coil) during stretching and the resulting higher transmitted energy in the heater. The heating process took approximately thirty (30) seconds to reach the desired temperature for both unstretched/non-strained and stretched/strained heater (e.g., see graph 2000 in FIG. 20 which shows time-dependent temperature profiles for the unstretched heater and the stretched heater). The results illustrated the potential utility of the textile integrated wearable wireless heater for therapeutic heating.

Thus, some embodiments of the disclosed subject matter presents facile textile integration of AgNW/TPU nanocomposites for multifunctional E-textiles based on laser direct scribing and heat press lamination. A minimal linewidth of 135 µm and sheet resistance of 0.2 Ω/sq were achieved for the laminated AgNW/TPU patterns on textile materials. The increase in resistance was found to be less than 6% under tensile strain up to 30%. The integrated textiles exhibited comparable mechanical properties to the original textiles, and stable electrical performance after many cycles of washing. A fully integrated patch comprising of four dry electrophysiological electrodes, a capacitive strain sensor, and a wireless heater was designed and fabricated. The results demonstrated the capability of ECG/EMG sensing, body motion sensing, and thermotherapy in a single wearable textile patch, which are all of important relevance to sports applications. For example, the textile patch (and/or sports tape embodiment) can be used to gather data from various joints (e.g., elbow, wrist, shoulder, knee, etc.) involved in a sports-related motion (e.g., baseball throw, a golf swing, a basketball shot, etc.). Features like excellent electrical performance, wearability, and washability promise the wide applications of the multifunctional E-textiles. For example, the collected physiological and body activity parameters can provide valuable insights into the well-being and fitness of the human body. Example use cases include areas such as physical therapy, physical rehabilitation, sports analytics, and the like. The E-textiles offer a convenient tool to quantify body motions and provide feedback for prosthetics and robotics. In addition to the functions demonstrated in this work, other wearable functions such as touch, skin impedance, and an antenna can be readily integrated into textile materials using this technique.

Experimental Section

Textile integration of AgNW based nanocomposites: The synthesis of AgNWs followed a modified polyol reduction method with slight modifications. The synthesized nanowires were dispersed into ethanol for the subsequent coating process. The glass substrate was treated with release agent (Ease Release® 200, Smooth-on) to help detach with the AgNW/TPU in the heat press process. AgNW solution was coated onto the glass substrate using Meyer rod coating followed by drying at 50° C. on a hotplate. More cycles of coating and drying were performed to achieve the desired AgNW density. TPU solution (0.25 g/ml TPU (Perfectex plus LLC)) dispersed in dimethylformamide (DMF) was then spin coated over the AgNWs at 250 revolutions per minute (rpm) for 30 seconds. The solvent was evaporated at 120° C. on a hotplate for one hour to embed the AgNWs into TPU. Next, the AgNW/TPU nanocomposites were patterned into desired shapes using a laser cutter (Universal VLS 6.60, Epilog Laser) with a cutting speed of 100% and power of 10%. The patterns were subsequently pressed at 140° C. onto stretchable textiles using a digital heat press machine (Fancierstudio). After removing the glass substrate, AgNW/TPU patterns were transferred onto the textiles. Laminated patterns on both sides were electrically connected by Ag stretchable printing ink.

Characterization of AgNW/TPU laminated textiles: Stress-strain curves of the textile with and without AgNW/TPU patterns were obtained using a mechanical tester (DTS Company) at a loading speed of 0.05 mm s$^{-1}$. For electromechanical testing, the textiles were mounted onto a lab-made tensile stage and subjected to cycles of stretching and releasing. Meanwhile, the resistance of the AgNW/TPU patterns on textiles under strain was measured by a digital multimeter (34401A, Agilent). ECG and EMG measurements were performed using an amplifier (PowerLab 4/26, ADInstruments) with a sampling rate of 1 kHz per channel. The electrode-skin impedance was measured using a potentiostat (Reference 600, Gamry Instruments). To test the heating performance, the wireless heater was powered by a commercial Qi wireless charger (Armike Inc.). The temperature of the heater was obtained in real time with an infrared camera (A655SC FLIR) placed right over the heater. The capacitance of the fabricated capacitive strain sensors was measured using a capacitance-to-digital converter evaluation board (AD7152, Analog Devices) with a sampling frequency of 50 Hz. To measure the gauge factor, the strain sensor was stretched on a tensile stage, with the capacitance measured at the same time. The washability of the fabricated electronic textiles was tested according to the international standard ISO 6330:2000. The samples were placed in a laundry bag with 2 kg of ballast to reach 2 kg standard load. The "delicate" option was chosen for the washing process. Between each washing cycle, the samples were drip dry at room temperature. The resistance of the AgNW/TPU pattern on textiles was measured after every 5 cycles.

Figure 25:
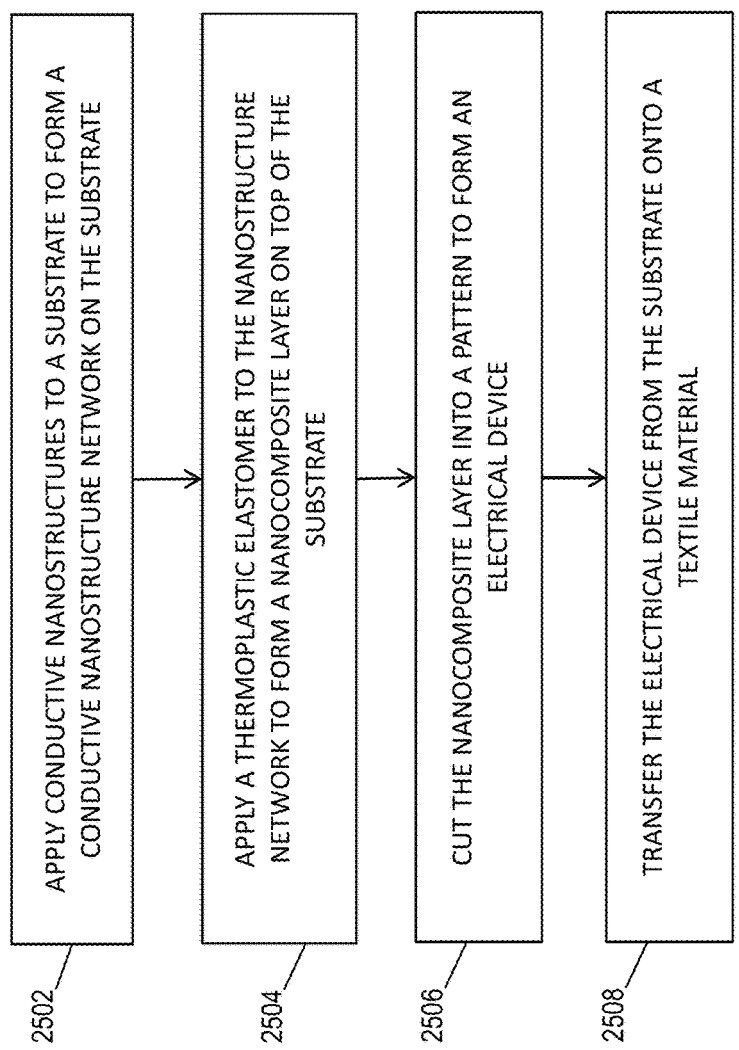
FIG. 25 is a flow chart illustrating an exemplary process for producing a textile product with an integrated electrical device according to an embodiment of the subject matter described herein.

FIG. 25 is a diagram illustrating an exemplary method and/or process 2500 for producing a textile product with an integrated electrical device according to an embodiment of the subject matter described herein.

In block 2502, conductive nanostructures are applied to a substrate to form a conductive nanostructures network on the substrate. In some embodiments, an ethanol solution containing a multitude of nanostructures, such as nanowires, is applied as a layer onto a substrate, such as glass substrate. As such, the plurality of nanostructures will be positioned on the entirety of the glass substrate thereby forming a nanostructure network (e.g., a conductive nanowire network). Notably, the nanostructures can be made of silver, copper, or gold.

In block 2504, a thermoplastic elastomer is applied to the nanowire network to form a nanocomposite layer on top of the substrate. In some embodiments, a layer of thermoplastic elastomer (e.g., TPU) solution can be coated, sprayed, or poured on top of the previously applied layer of nanostructures (e.g., the conductive nanowire network). The resulting composition of these two layers forms a nanocomposite layer that is positioned on top of the glass substrate.

In block 2506, the nanocomposite layer is cut into a desired pattern to form an electrical device. In some embodiments, a laser scribe or other cutting device is used to cut a design (e.g., a desired pattern) to form an electrical device (e.g., a nanocomposite pattern element). The electrical device is still adhered to the glass substrate at this stage.

In block 2508, the electrical device is transferred from the substrate onto a textile fabric. In some embodiments, the electrical device (e.g., nanocomposite pattern element) can be applied to a textile material or textile fabric. For example, the thermoplastic elastomer portion of the electrical device is thermal sensitive and can be rendered to adhere to the textile fabric upon the application of heat and pressure. Notably, the electrical device can be positioned on top of the textile material (e.g., the textile material being unstretched or the textile material can be stretched prior to and during the laminating of the electrical device onto the textile material) and have pressure and heat applied in a manner that permits the electrical device (e.g., nanocomposite pattern element) to transfer and adhere to the textile material (i.e., an integrated electrical device patch).

It will be appreciated that exemplary process 2500 is for illustrative purposes only and that different and/or additional actions may be used. It will also be appreciated that various actions associated with exemplary process 2500 may occur in a different order or sequence.

It will be understood that various details of the subject matter described herein may be changed without departing from the scope of the subject matter described herein. Furthermore, the foregoing description is for the purpose of illustration only, and not for the purpose of limitation. For example, various combinations and sub-combinations of the structures and features described herein are contemplated and will be apparent to a skilled person having knowledge of this disclosure. Any of the various features and elements as disclosed herein can be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims.

REFERENCES

All references listed in the instant disclosure, including but not limited to all patents, patent applications and publications thereof, scientific journal articles, and database entries are incorporated herein by reference in their entireties to the extent that they supplement, explain, provide a background for, or teach methodology, techniques, and/or embodiments employed herein.

[1] J. A. Rogers, T. Someya, Y. Huang, *Science* 2010, 327, 1603.
[2] T. Q. Trung, N. E. Lee, *Adv. Mater.* 2016, 28, 4338.
[3] Y. Khan, A. E. Ostfeld, C. M. Lochner, A. Pierre, A. C. Arias, *Adv. Mater.* 2016, 28, 4373.
[4] S. Yao, P. Swetha, Y. Zhu, *Adv. Healthc. Mater.* 2018, 7, 1700889.
[5] T. Wang, H. Yang, D. Qi, Z. Liu, P. Cai, H. Zhang, X. Chen, *Small* 2018, 14, 1702933.
[6] S. Gong, W. Cheng, *Adv. Electron. Mater.* 2017, 3, 1600314.
[7] W. Gao, S. Emaminejad, H. Y. Y. Nyein, S. Challa, K. Chen, A. Peck, H. M. Fahad, H. Ota, H. Shiraki, D. Kiriya, D.-H. Lien, G. A. Brooks, R. W. Davis, A. Javey, *Nature* 2016, 529, 509.
[8] Z. Huang, Y. Hao, Y. Li, H. Hu, C. Wang, A. Nomoto, T. Pan, Y. Gu, Y. Chen, T. Zhang, W. Li, Y. Lei, N. Kim, C. Wang, L. Zhang, J. W. Ward, A. Maralani, X. Li, M. F. Durstock, A. Pisano, Y. Lin, S. Xu, *Nat. Electron.* 2018, 1, 473.
[9] D. Son, J. Kang, O. Vardoulis, Y. Kim, N. Matsuhisa, J. Y. Oh, J. W. To, J. Mun, T. Katsumata, Y. Liu, A. F. McGuire, M. Krason, F. Molina-Lopez, J. Ham, U. Kraft, Y. Lee, Y. Yun, J. B.-H. Tok, Z. Bao, *Nat. Nanotechnol.* 2018, 13, 1057.
[10] H.-J. Kim, K. Sim, A. Thukral, C. Yu, *Sci. Adv.* 2017, 3, e1701114.
[11] S. Lim, D. Son, J. Kim, Y. B. Lee, J. K. Song, S. Choi, D. J. Lee, J. H. Kim, M. Lee, T. Hyeon, D.-H. Kim, *Adv. Funct. Mater.* 2015, 25, 375.
[12] X. Wang, Y. Zhang, X. Zhang, Z. Huo, X. Li, M. Que, Z. Peng, H. Wang, C. Pan, *Adv. Mater.* 2018, 30, 1706738.
[13] H. Lee, T. K. Choi, Y. B. Lee, H. R. Cho, R. Ghaffari, L. Wang, H. J. Choi, T. D. Chung, N. Lu, T. Hyeon, S. H. Choi, D.-H. Kim, *Nat. Nanotechnol.* 2016, 11, 566.
[14] D.-H. Kim, N. Lu, R. Ma, Y.-S. Kim, R.-H. Kim, S. Wang, J. Wu, S. M. Won, H. Tao, A. Islam, K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, *Science* 2011, 333, 838.
[15] B. Sun, R. N. McCay, S. Goswami, Y. Xu, C. Zhang, Y. Ling, J. Lin, Z. Yan, *Adv. Mater.* 2018, 30, 1804327.
[16] A. Miyamoto, S. Lee, N. F. Cooray, S. Lee, M. Mori, N. Matsuhisa, H. Jin, L. Yoda, T. Yokota, A. Itoh, *Nat. Nanotechnol.* 2017, 12, 907.
[17] L. M. Castano, A. B. Flatau, *Smart Mater. Struct.* 2014, 23, 053001.
[18] J. S. Heo, J. Eom, Y. H. Kim, S. K. Park, *Small* 2018, 14, 1703034.
[19] W. Zeng, L. Shu, Q. Li, S. Chen, F. Wang, X. M. Tao, *Adv. Mater.* 2014, 26, 5310.
[20] N. Matsuhisa, M. Kaltenbrunner, T. Yokota, H. Jinno, K. Kuribara, T. Sekitani, T. Someya, *Nat. Commun.* 2015, 6, ncomms8461.
[21] R. Cao, X. Pu, X. Du, W. Yang, J. Wang, H. Guo, S. Zhao, Z. Yuan, C. Zhang, C. Li, Z. L. Wang, *ACS Nano* 2018, 12, 5190.
[22] M. A. Yokus, R. Foote, J. S. Jur, *IEEE Sens. J.* 2016, 16, 7967.
[23] H. Jin, N. Matsuhisa, S. Lee, M. Abbas, T. Yokota, T. Someya, *Adv. Mater.* 2017, 29, 1605848.
[24] K. Wills, K. Krzyzak, J. Bush, R. Ashayer-Soltani, J. Graves, C. Hunt, A. Cobley, *J. Text. I.* 2018, 109, 268.
[25] J. Suikkola, T. Björninen, M. Mosallaei, T. Kankkunen, P. Iso-Ketola, L. Ukkonen, J. Vanhala, M. Mäntysalo, *Sci. Rep.* 2016, 6, 25784.
[26] T. Vervust, G. Buyle, F. Bossuyt, J. J. J. o. T. T. I. Vanfleteren, *J. Text. I.* 2012, 103, 1127.
[27] K.-I. Jang, S. Y. Han, S. Xu, K. E. Mathewson, Y. Zhang, J.-W. Jeong, G.-T. Kim, R. C. Webb, J. W. Lee, T. Dawidczyk, R. H. Kim, Y. M. Song, W.-H. Yeo, S. Kim, H. Cheng, S. I. Rhee, J. Chung, B. Kim, H. U. Chung, D. Lee, Y. Yang, M. Cho, J. G. Gaspar, R. Carbonari, M. Fabiani, G. Gratton, Y. Huang, J. A. Rogers, *Nat. Commun.* 2014, 5, 4779.
[28] Q. Huang, K. N. Al-Milaji, H. Zhao, *ACS Appl. Nano Mater.* 2018, 1, 4528.
[29] Q. Huang, Y. Zhu, *Sci. Rep.* 2017, 8, 15167.
[30] J. Liang, K. Tong, Q. Pei, *Adv. Mater.* 2016, 28, 5986.
[31] Z. Cui, Y. Han, Q. Huang, J. Dong, Y. Zhu, *Nanoscale* 2018, 10, 6806.
[32] H. Lee, B. Seong, J. Kim, Y. Jang, D. Byun, *Small* 2014, 10, 3918.
[33] T. Tokuno, M. Nogi, M. Karakawa, J. Jiu, T. T. Nge, Y. Aso, K. Suganuma, *Nano Res.* 2011, 4, 1215.
[34] D. Langley, M. Lagrange, G. Giusti, C. Jimenez, Y. Bréchet, N. D. Nguyen, D. Bellet, *Nanoscale* 2014, 6, 13535.
[35] F. Xu, Y. Zhu, *Adv. Mater.* 2012, 24, 5117.
[36] S. Yao, Y. Zhu, *Adv. Mater.* 2015, 27, 1480.
[37] J. A. Fan, W.-H. Yeo, Y. Su, Y. Hattori, W. Lee, S.-Y. Jung, Y. Zhang, Z. Liu, H. Cheng, L. Falgout, M. Bajema, T. Coleman, D. Gregoire, R. J. Larsen, Y. Huang, J. A. Rogers, *Nat. Commun.* 2014, 5, 3266.
[38] X. Tao, T. H. Huang, C. L. Shen, Y. C. Ko, G. T. Jou, V. Koncar, *Adv. Mater. Technol.* 2018, 3, 1700309.
[39] L. Yu, J. C. Yeo, R. H. Soon, T. Yeo, H. H. Lee, C. T. Lim, *ACS Appl. Mater. Interfaces* 2018, 10, 12773.
[40] Z. Zhao, C. Yan, Z. Liu, X. Fu, L. M. Peng, Y. Hu, Z. Zheng, *Adv. Mater.* 2016, 28, 10267.
[41] X. Tao, V. Koncar, T.-H. Huang, C.-L. Shen, Y.-C. Ko, G.-T. Jou, *Sensors* 2017, 17, 673.
[42] A. Ankhili, X. Tao, C. Cochrane, D. Coulon, V. Koncar, *Materials* 2018, 11, 256.

[43] S. Yao, Y. Zhu, *JOM* 2016, 68, 1145.
[44] S. Yao, Y. Zhu, *Nanoscale* 2014, 6, 2345.
[45] S. Yao, L. Vargas, Y. Zhu, X. Hu, *IEEE Sens. J.* 2017, 18, 3010.
[46] M. Amjadi, K. U. Kyung, I. Park, M. Sitti, *Adv. Fund. Mater.* 2016, 26, 1678.
[47] H. Nakamoto, H. Ootaka, M. Tada, I. Hirata, F. Kobayashi, F. Kojima, *IEEE Sens. J.* 2016, 16, 3572.
[48] M. Dehghan, F. FarahbOD, *J. Clin. Diagn. Res.* 2014, 8, LC01.
[49] G. A. Malanga, N. Yan, J. Stark, *Postgrad. Med.* 2015, 127, 57.
[50] R. Rahimi, S. Shams Es-haghi, S. Chittiboyina, Z. Mutlu, S. A. Lelièvre, M. Cakmak, B. Ziaie, *Adv. Healthc. Mater.* 2018, 7, 1800231.
[51] S. Han, M. K. Kim, B. Wang, D. S. Wie, S. Wang, C. H. Lee, *Adv. Mater.* 2016, 28, 10257.
[52] K. Okada, T. Yamaguchi, K. Minowa, N. Inoue, *J. Oral. Rehabil.* 2005, 32, 480.
[53] S. Yao, J. Cui, Z. Cui, Y. Zhu, *Nanoscale* 2017, 9, 3797.
[54] P.-C. Hsu, X. Liu, C. Liu, X. Xie, H. R. Lee, A. J. Welch, T. Zhao, Y. Cui, *Nano Lett.* 2014, 15, 365.
[55] Z. Cui, F. R. Poblete, G. Cheng, S. Yao, X. Jiang, Y. Zhu, *J. Mater. Res.* 2015, 30, 79.
[56] S. Yao, A. Myers, A. Malhotra, F. Lin, A. Bozkurt, J. F. Muth, Y. Zhu, *Adv. Healthc. Mater.* 2017, 6, 1601159.
[57] L. Song, A. C. Myers, J. J. Adams, Y. Zhu, *Appl. Mater. Interfaces* 2014, 6, 4248.

What is claimed is:

1. A textile material product with an integrated electrical device, the textile material product comprising:
a textile material; and
an electrical device comprising a patch laminated to the textile material, wherein the electrical device comprises a network of silver nanowires forming a layer and coated with a thermoplastic polyurethane (TPU) to form a nanocomposite layer, which is cut into a pattern to form an electrical device, wherein the network of silver nanowires extends to an edge of the TPU of the electrical device, and wherein the electrical device is bonded to the textile material to form an electronically integrated textile product, wherein the pattern comprises one of a coil pattern and a fractal pattern.

2. The textile material product of claim 1 wherein the textile material comprises a stretchable fabric.

3. The textile material product of claim 1 wherein the electrical device comprises a sensor device.

4. The textile material product of claim 3 wherein the sensor device comprises at least one of a capacitive strain gauge, an angular velocity sensor, an electrocardiogramansor, or an electromyography sensor.

5. The textile material product of claim 1 wherein the nanocomposite layer is formed via a curing of the thermoplastic elastomer around the nanostructure network.

6. The textile material product of claim 1 wherein the electrical device comprises a resistive heater.

7. The textile material product of claim 1 wherein the electrical device is heat press laminated to the textile material.

8. The textile material product of claim 1 wherein the pattern comprises the coil pattern.

9. The textile material product of claim 1 wherein the pattern comprises the fractal pattern.

* * * * *